United States Patent
Lindenmann et al.

(10) Patent No.: US 11,117,197 B2
(45) Date of Patent: Sep. 14, 2021

(54) INSTRUMENT COUPLINGS AND RELATED METHODS

(71) Applicant: Medos International Sarl, Le Locle (CH)

(72) Inventors: Philippe Lindenmann, Basel (CH); Felix Aschmann, Basel (CH); Daniela Wehrli, Wangen bei Olten (CH)

(73) Assignee: MEDOS INTERNATIONAL SARL, Le Locle (CH)

( * ) Notice: Subject to any disclaimer, the term of this patent is extended or adjusted under 35 U.S.C. 154(b) by 52 days.

(21) Appl. No.: 15/609,702

(22) Filed: May 31, 2017

(65) Prior Publication Data

US 2018/0344304 A1    Dec. 6, 2018

(51) Int. Cl.
B23B 31/107    (2006.01)
B23B 31/22    (2006.01)
(Continued)

(52) U.S. Cl.
CPC ........ B23B 31/1072 (2013.01); B23B 31/223 (2013.01); *A61B 17/00234* (2013.01);
(Continued)

(58) Field of Classification Search
CPC ..... B23B 2231/32; B23B 31/22; B23B 31/19; B23B 31/223; B23B 31/1072; B23B 31/1071; B23B 31/1078; B23B 31/003; Y10T 279/3481; Y10T 279/17752; Y10T 279/17811

See application file for complete search history.

(56) References Cited

U.S. PATENT DOCUMENTS 3,251,605 A * 5/1966 Ondeckelmerj .... B23B 31/1071
                                                          279/82
4,828,277 A * 5/1989 De Bastiani ............ B23B 31/22
                                                         279/133

(Continued)

FOREIGN PATENT DOCUMENTS

DE        19636293 A1 *  3/1997  .......... B25D 17/088
EP        1537829 A1     6/2005

(Continued)

OTHER PUBLICATIONS

International Search Report and Written Opinion dated Oct. 10, 2018 for Application No. PCT/EP18/64251 (12 pages).

(Continued)

*Primary Examiner* — Eric A. Gates
*Assistant Examiner* — Paul M Janeski
(74) *Attorney, Agent, or Firm* — Barnes & Thornburg LLP

(57) ABSTRACT

Instrument couplings and related methods are disclosed herein, e.g., for coupling a surgical instrument to a navigation array or other component. The coupling can reduce or eliminate movement between the instrument and the navigation array, improving navigation precision. The coupling can be quick and easy to use, reducing or eliminating the need for extra steps or additional tools to attach or detach the instrument from the coupling. In some embodiments, the single step of inserting an instrument into the coupling can automatically lock the instrument within the coupling in a toggle-free manner.

27 Claims, 17 Drawing Sheets

(51) Int. Cl.

| | | |
|---|---|---|
| A61B 17/00 | (2006.01) | |
| A61B 90/00 | (2016.01) | |
| A61B 34/20 | (2016.01) | |
| A61B 17/88 | (2006.01) | |
| B23B 31/19 | (2006.01) | |

(52) U.S. Cl.
CPC .......... *A61B 17/88* (2013.01); *A61B 17/8819* (2013.01); *A61B 34/20* (2016.02); *A61B 90/39* (2016.02); *A61B 2017/00477* (2013.01); *A61B 2034/2055* (2016.02); *A61B 2090/034* (2016.02); *A61B 2090/3983* (2016.02); *B23B 31/19* (2013.01); *B23B 31/22* (2013.01)

(56) References Cited

U.S. PATENT DOCUMENTS

| | | | |
|---|---|---|---|
| 5,211,576 | A | 5/1993 | Tonkiss et al. |
| 6,190,395 | B1 | 2/2001 | Williams |
| 6,270,087 | B1 | 8/2001 | Mickel et al. |
| 6,434,507 | B1 | 8/2002 | Clayton et al. |
| 6,530,579 | B1 * | 3/2003 | Houben ............... B23D 51/08 279/30 |
| 6,556,857 | B1 | 4/2003 | Estes et al. |
| 6,932,823 | B2 | 8/2005 | Grimm et al. |
| 7,043,961 | B2 | 5/2006 | Pandey et al. |
| 7,153,308 | B2 | 12/2006 | Peterson |
| 7,166,114 | B2 | 1/2007 | Moctezuma De La Barrera et al. |
| 7,226,456 | B2 | 6/2007 | O'Neil et al. |
| 7,274,958 | B2 | 9/2007 | Jutras et al. |
| 7,289,227 | B2 | 10/2007 | Smetak et al. |
| 7,314,048 | B2 | 1/2008 | Couture et al. |
| 7,458,977 | B2 | 12/2008 | McGinley et al. |
| 7,668,584 | B2 | 2/2010 | Jansen |
| 7,688,998 | B2 | 3/2010 | Tuma et al. |
| 7,873,400 | B2 | 1/2011 | Moctezuma De La Barrera et al. |
| 7,877,890 | B2 | 2/2011 | Weber |
| 7,993,353 | B2 | 8/2011 | Ro.beta.ner et al. |
| 8,216,211 | B2 | 7/2012 | Mathis et al. |
| 8,303,596 | B2 | 11/2012 | Pla.beta.ky et al. |
| 8,386,022 | B2 | 2/2013 | Jutras et al. |
| 8,419,750 | B2 | 4/2013 | Kienzle, III et al. |
| 8,509,878 | B2 | 8/2013 | Pfeifer et al. |
| 8,560,047 | B2 | 10/2013 | Haider et al. |
| 8,688,196 | B2 | 4/2014 | Whitmore, III et al. |
| 8,734,432 | B2 | 5/2014 | Tuma et al. |
| 8,764,025 | B1 * | 7/2014 | Gao .................. B23B 31/1071 279/22 |
| 8,800,939 | B2 | 8/2014 | Karsak et al. |
| 8,821,511 | B2 | 9/2014 | von Jako et al. |
| 8,834,455 | B2 | 9/2014 | Kleven |
| 8,882,113 | B2 * | 11/2014 | Porter .................. A61C 1/142 279/155 |
| 8,961,500 | B2 | 2/2015 | Dicorleto et al. |
| 8,961,536 | B2 | 2/2015 | Nikou et al. |
| 8,985,593 | B1 * | 3/2015 | Gao .................. A61B 17/162 279/74 |
| RE45,484 | E | 4/2015 | Foley et al. |
| 9,005,211 | B2 | 4/2015 | Brundobler et al. |
| 9,232,985 | B2 | 1/2016 | Jacobsen et al. |
| 9,265,589 | B2 | 2/2016 | Hartmann et al. |
| 9,873,155 | B1 * | 1/2018 | Wienhold .......... B23B 31/1071 |
| 10,722,223 | B2 | 7/2020 | Wehrli et al. |
| 2004/0054489 | A1 | 3/2004 | Moctezuma De La Barrera et al. |
| 2004/0077940 | A1 | 4/2004 | Kienzle et al. |
| 2004/0138588 | A1 | 7/2004 | Saikley |
| 2004/0171930 | A1 | 9/2004 | Grimm et al. |
| 2005/0049485 | A1 | 3/2005 | Harmon et al. |
| 2005/0124988 | A1 | 6/2005 | Terrill-Grisoni et al. |
| 2005/0154296 | A1 | 7/2005 | Lechner et al. |
| 2005/0203539 | A1 | 9/2005 | Grimm et al. |
| 2006/0052691 | A1 | 3/2006 | Hall et al. |
| 2007/0225725 | A1 | 9/2007 | Heavener et al. |
| 2010/0160932 | A1 | 6/2010 | Gschwandtner et al. |
| 2011/0263971 | A1 | 10/2011 | Nikou et al. |
| 2012/0232377 | A1 | 9/2012 | Nottmeier |
| 2013/0172907 | A1 | 7/2013 | Harris |
| 2013/0178745 | A1 | 7/2013 | Kyle, Jr. et al. |
| 2014/0257332 | A1 | 9/2014 | Zastrozna |
| 2014/0276007 | A1 | 9/2014 | Sela et al. |
| 2014/0371728 | A1 | 12/2014 | Vaughn |
| 2015/0042052 | A1 | 2/2015 | Furusawa et al. |
| 2015/0102567 | A1 * | 4/2015 | Chan .................. B25B 23/0035 279/75 |
| 2015/0182293 | A1 | 7/2015 | Yang et al. |
| 2015/0265260 | A1 | 9/2015 | Knodel et al. |
| 2015/0265769 | A1 | 9/2015 | Bratbak et al. |
| 2015/0305817 | A1 | 10/2015 | Kostrzewski |
| 2015/0362828 | A1 | 12/2015 | Patel et al. |
| 2016/0015374 | A1 | 1/2016 | Gifford et al. |
| 2016/0030129 | A1 | 2/2016 | Christian et al. |
| 2018/0008354 | A1 | 1/2018 | Nguyen et al. |
| 2018/0344301 | A1 | 12/2018 | Wehrli et al. |
| 2020/0323521 | A1 | 10/2020 | Wehrli et al. |

FOREIGN PATENT DOCUMENTS

| | | |
|---|---|---|
| EP | 2 793 728 A1 | 10/2014 |
| WO | 02/11620 A1 | 2/2000 |
| WO | 2013115640 A1 | 8/2013 |
| WO | 2014/003848 A1 | 1/2014 |
| WO | 2016023599 A1 | 2/2016 |

OTHER PUBLICATIONS

International Search Report and Written Opinion for Application No. PCT/EP2018/064268, dated Dec. 18, 2018 (19 pages).
International Preliminary Report on Patentability for Application No. PCT/EP2018/064268, dated Dec. 12, 2019 (14 pages).

* cited by examiner

Toggle

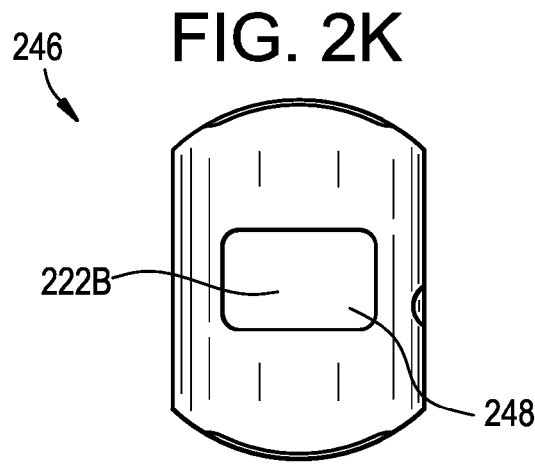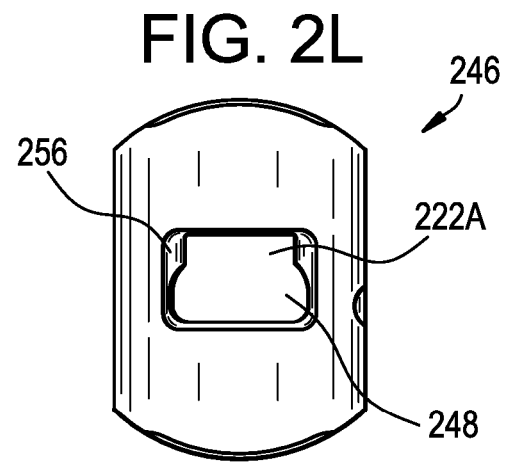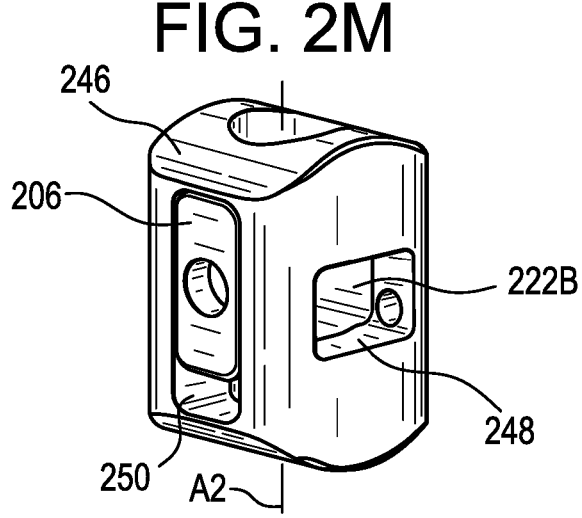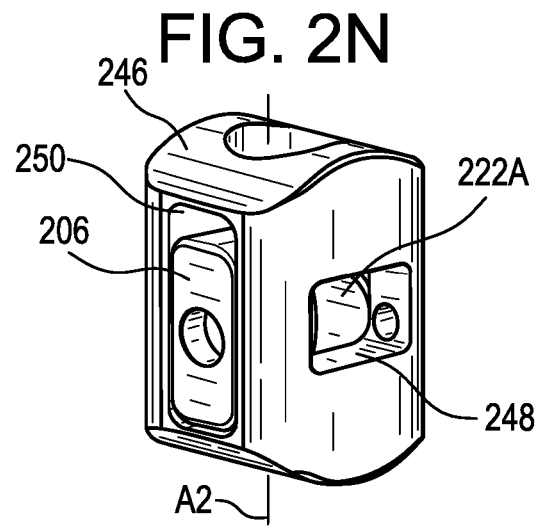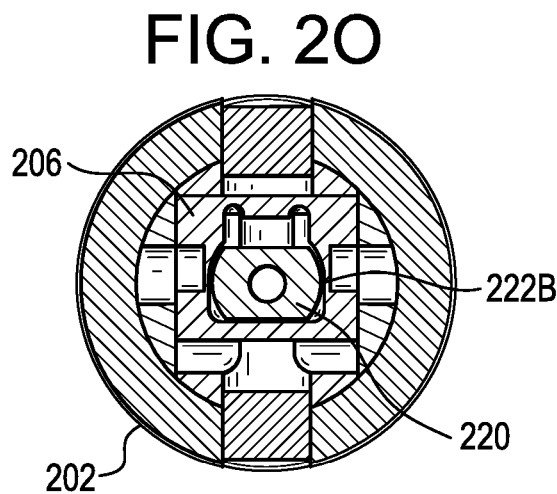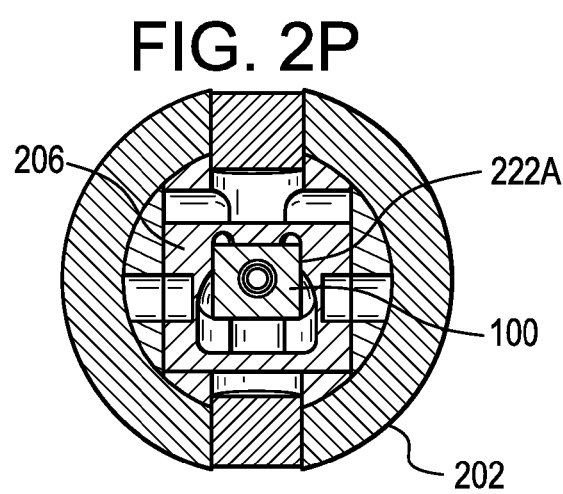

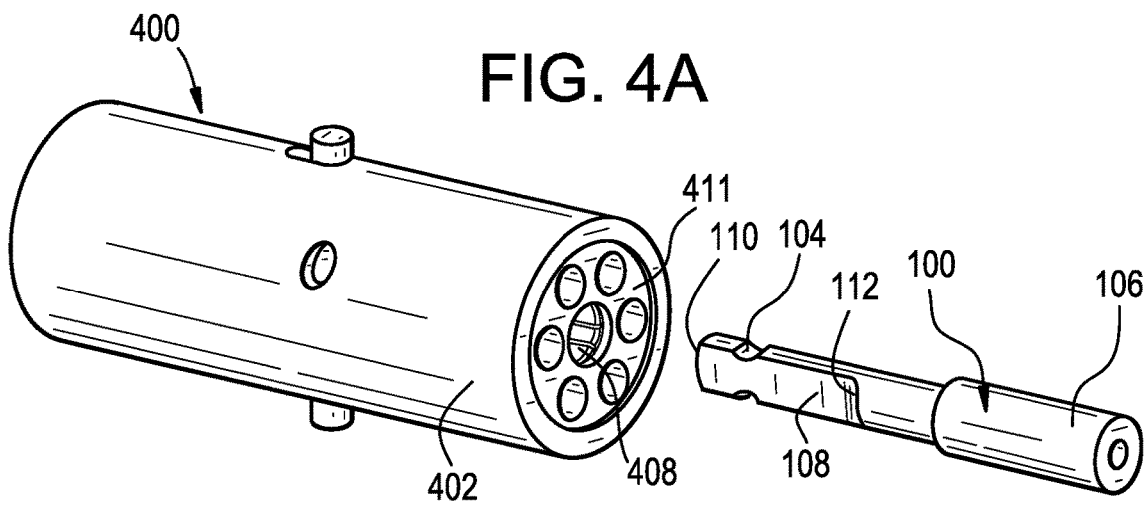
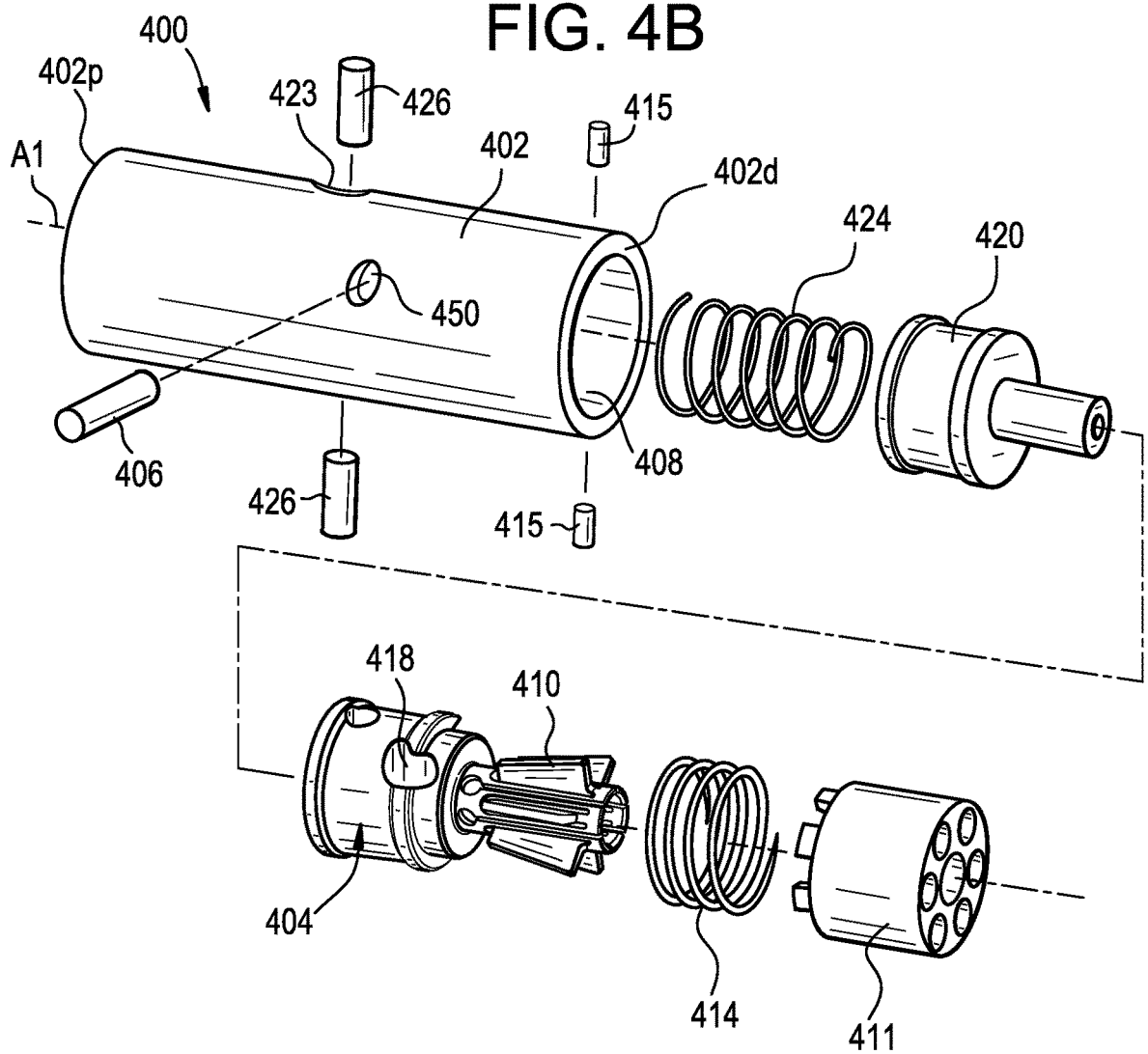

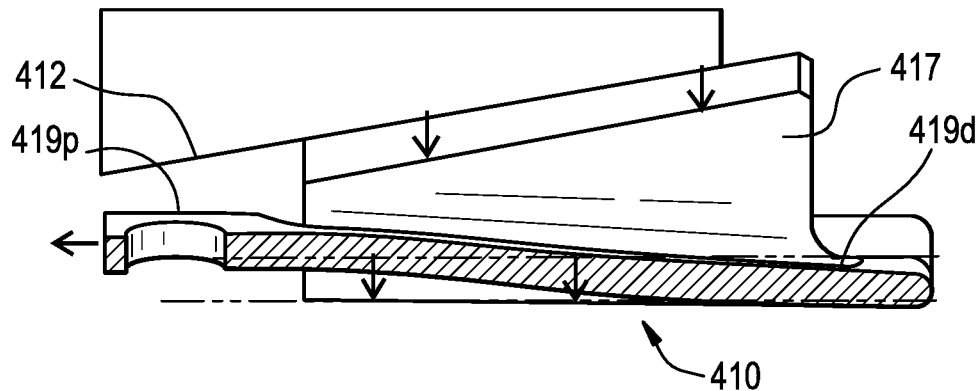
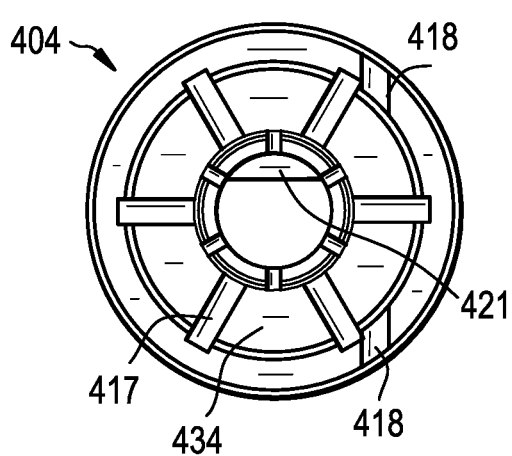 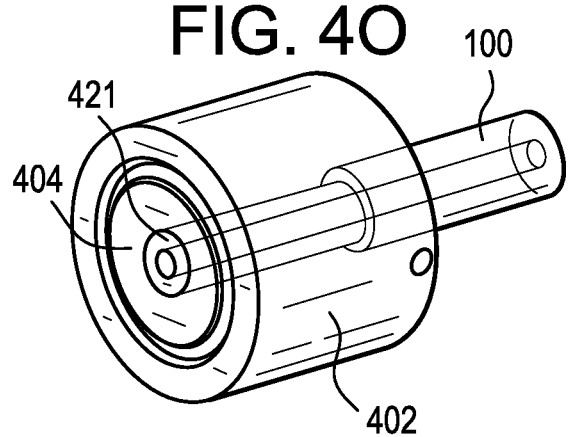
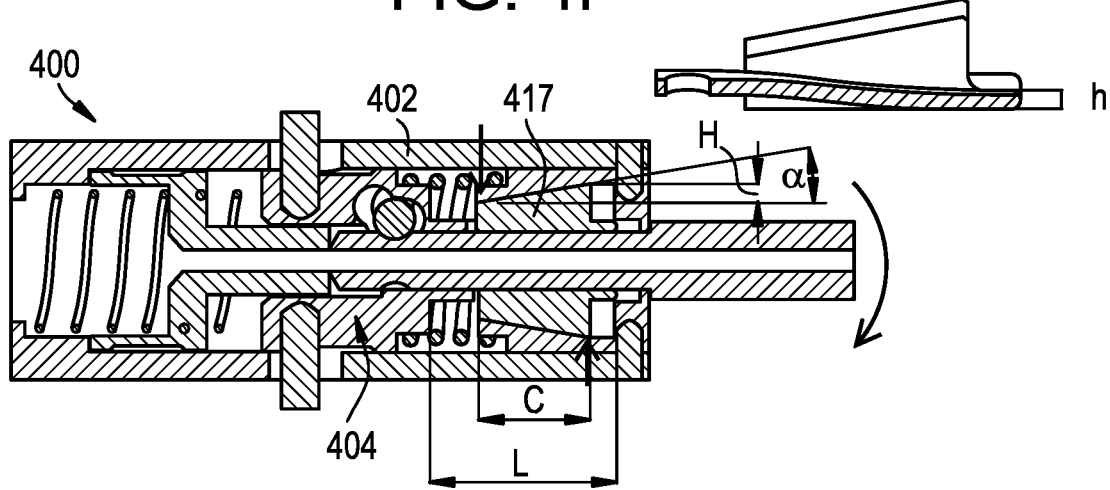

INSTRUMENT COUPLINGS AND RELATED METHODS

FIELD

Instrument couplings and related methods are disclosed herein, e.g., for coupling a surgical instrument to a navigation array or other component.

BACKGROUND

It is increasingly common for surgical procedures to involve navigation or tracking of instruments used during the surgery. Surgical navigation can be helpful in avoiding delicate neural or vascular structures when moving implants or instruments within a patient. In spinal surgery, for example, a surgical navigation system can be used during screw insertion, disc removal, bone preparation, and other steps of the surgery. Use of surgical navigation systems can also reduce the amount of X-ray exposure to which the patient and operating room staff are exposed.

A typical navigation system includes an array of markers attached to a surgical instrument, an imaging system that captures images of the surgical field, and a controller that detects the markers in the captured images and tracks movement of the markers within the surgical field. The controller associates a reference frame of the imaging system with a reference frame of the patient and, informed by a known geometry of the array and the instrument, determines how the instrument is being moved relative to the patient. Based on that determination, the controller provides navigation feedback to the surgeon.

The precision of the navigation system is strongly dependent on the design of the navigated instrument. When the navigation array is welded to the instrument or integrally-formed with the instrument, relatively high precision can be achieved. Such arrangements can be inconvenient, however, as the capability to remove the array from the instrument or to attach the array to other instruments is lacking. Further, arrangements having the navigation array integrally-formed with the instrument can require separate instruments for standard and navigation use, thereby raising costs for equipment.

A number of modular systems have been developed to allow the navigation array to be interchangeably attached with one or more instruments. These systems can be cumbersome to use, often requiring two hands, numerous steps, and/or additional tools to attach the array to the instrument and to remove the array from the instrument. These systems can also allow for considerable "play" between the instrument and the array, which can undesirably reduce the precision of the navigation. For example, as shown in FIG. 1, a traditional ring-type coupling can undesirably allow the instrument to toggle relative to the array, introducing navigation error. Various types of movement between the instrument and the array (e.g., heave, sway, pitch, yaw, roll, and/or surge) can introduce navigation error.

SUMMARY

Instrument couplings and related methods are disclosed herein, e.g., for coupling a surgical instrument to a navigation array or other component. The coupling can reduce or eliminate movement between the instrument and the navigation array, improving navigation precision. The coupling can be quick and easy to use, reducing or eliminating the need for extra steps or additional tools to attach or detach the instrument from the coupling. In some embodiments, the single step of inserting an instrument into the coupling can automatically lock the instrument within the coupling in a toggle-free manner.

In some embodiments, a coupling device can include a housing having proximal and distal ends and a central longitudinal axis A1 extending therebetween; and a clamp having a plurality of clamping elements and defining an instrument channel, the clamp being longitudinally-slidable within the housing between an unclamped position in which the clamping elements are free to move radially outward away from the axis A1 and a clamped position in which the clamping elements are urged radially-inward towards the axis A1.

The coupling device can include a slider movable relative to the housing between a first position in which an engagement feature of the slider is disposed in the instrument channel and a second position in which the engagement feature is offset from the instrument channel. The slider in the first position can maintain the clamp in the unclamped position and the slider in the second position can allow the clamp to move to the clamped position. The slider can be movable between the first and second positions by translating the slider relative to the housing along an axis A2 that is perpendicular to the axis A1. The slider can include a pin received within a slot formed in the clamp. The slot can include a sloped portion that extends at an oblique angle relative to the axis A1 and a non-sloped portion that extends parallel to the axis A1. The engagement feature of the slider can include a protrusion formed in an opening of the slider, the opening being configured to receive an instrument therethrough when the instrument is inserted into the coupling. The engagement feature of the slider can include an exterior surface of the slider. The slider can be mounted in a slider cage, the slider cage being longitudinally-translatable within a cavity of the clamp and being longitudinally-fixed relative to the housing. The slider can be mounted in a transverse throughbore of the housing. The coupling device can include an ejector configured to eject an instrument from the instrument channel. The coupling device can include an ejector that holds the slider in the first position when no instrument is inserted in the instrument channel. Insertion of an instrument into the instrument channel can displace the ejector to allow the slider to move to the second position. The ejector can be biased towards the slider by an ejector spring. The slider can include an opening having: a first portion with a width W1 large enough to allow the ejector to enter the opening when the first portion is aligned with the instrument channel; and a second portion with a width W2 that is less than the width W1, the second portion including a protrusion that defines the engagement feature of the slider and that is configured to engage an instrument disposed in the instrument channel when the second portion is aligned with the instrument channel. The clamping elements can be urged radially-inward by an interior surface feature of the coupling. The surface feature can include a conical interior surface of the housing. The surface feature can include a plurality of discrete ramped portions spaced about the interior circumference of a nose inserted into the housing. The nose can include a plurality of reliefs spaced about the interior circumference of the nose, the reliefs allowing the nose to be passed longitudinally over the clamping elements without moving the clamping elements. The plurality of clamping elements can include at least one of: (i) a roller having an axle supported by a cage portion of the clamp; (ii) a spherical ball supported by a cage portion of the clamp; and (iii) a chuck jaw slidably mounted in a track formed in the housing, the track having a central longitudinal axis that extends at an oblique angle relative to the axis A1. The plurality of clamping elements can include a finger that projects distally from a cage portion of the clamp, the finger having a radially-extending fin with a ramped contact surface. Movement of the clamp between the unclamped and clamped positions can cause parallel displacement of the fin relative to the axis A1. The finger can include a proximal flex portion at which the finger bends relative to the cage portion of the clamp and a distal flex portion at which the fin bends relative to the finger. The clamp can include a first cage portion in which a first plurality of the clamping elements are disposed and a second cage portion in which a second plurality of the clamping elements are disposed. The first and second cage portions can be longitudinally-translatable relative to one another. The first and second cage portions can be biased apart from one another along the axis A1. The housing can include a proximal ramped portion that urges the clamping elements of the first cage portion radially-inward and a distal ramped portion that urges the clamping elements of the second cage portion radially-inward. The clamp can be biased towards the clamped position by a clamp spring. The coupling device can include a release element to which a force can be applied along the axis A1 to move the clamp to the unclamped position. The coupling device can include an instrument configured to be selectively attached to the coupling, the instrument including a recess that is engaged by the slider when the instrument is received within the instrument channel to axially retain the instrument within the coupling. The coupling device can include a handle assembly in which the coupling is rotatably mounted. The handle assembly can include a bias element that biases the coupling distally along the axis A1 relative to the handle assembly. The handle assembly can include a locking element engaged with one or more teeth of the coupling to selectively maintain the coupling in a fixed rotational position about the axis A1 relative to the handle assembly.

In some embodiments, a coupling device can include a housing having an instrument channel and a clamp; wherein insertion of an instrument into the instrument channel causes the clamp to translate longitudinally within the housing to lock radial movement of the instrument relative to the housing.

The coupling device can include a slider, wherein insertion of an instrument into the instrument channel also causes the slider to translate laterally within the housing to lock axial movement of the instrument relative to the housing. The clamp can translate longitudinally within the housing to lock axial movement of the instrument relative to the housing.

In some embodiments, a method of attaching an instrument to a coupling can include inserting a portion of the instrument into an instrument channel of the coupling; translating a clamp longitudinally within a housing of the coupling to cause one or more clamping elements of the clamp to move radially-inward to clamp the instrument; and positioning an engagement feature of a slider within a corresponding engagement feature of the instrument to retain the instrument axially within the coupling.

Said translating of the clamp and said positioning of the engagement feature can occur automatically upon said insertion of the instrument. The method can include translating a release element longitudinally relative to the housing to release the instrument from the coupling. An ejector can automatically hold the coupling in an open position upon removal of the instrument from the coupling. Inserting the instrument can displace an ejector of the coupling to mobilize the slider and the clamp. Translating the clamp can include translating a first cage portion of the clamp a first distance and translating a second cage portion of the clamp a second distance that differs from the first distance. Translating the clamp can include carrying the clamping elements across a surface feature of the housing to urge the clamping elements radially-inward. Translating the clamp can include moving a pin of the slider along a slope slot of the clamp. Positioning the engagement feature of the slider can include at least one of: inserting a protrusion formed in an opening of the slider into a recess formed in the instrument; and inserting an exterior surface of the slider into a recess formed in the instrument. Positioning the engagement feature of the slider can include translating the slider relative to the housing along an axis that is perpendicular to a central longitudinal axis of the instrument channel.

BRIEF DESCRIPTION OF THE DRAWINGS

FIG. 2K is an end view of a slider cage and a slider of the coupling of FIG. 2A when the coupling is in an open position;

FIG. 2L is an end view of a slider cage and a slider of the coupling of FIG. 2A when the coupling is in a closed position;

FIG. 2M is a perspective view of a slider cage and a slider of the coupling of FIG. 2A when the coupling is in an open position;

FIG. 2N is a perspective view of a slider cage and a slider of the coupling of FIG. 2A when the coupling is in a closed position;

FIG. 2O is a transverse sectional view of the coupling of FIG. 2A when the coupling is in an open position;

FIG. 2P is a transverse sectional view of the coupling of FIG. 2A when the coupling is in a closed position;

FIG. 4A is a perspective view of a coupling and an instrument;

FIG. 4B is an exploded perspective view of the coupling of FIG. 4A;

FIG. 4M is side view of a clamping element of the clamp of FIG. 4J, shown in clamped and unclamped positions;

FIG. 4N is an end view of the clamp of FIG. 4J;

FIG. 4O is a sectional perspective view of the coupling of FIG. 4A with an instrument inserted into the coupling;

FIG. 4P is a sectional side view of the coupling of FIG. 4A with an instrument inserted into the coupling;

DETAILED DESCRIPTION

Instrument couplings and related methods are disclosed herein, e.g., for coupling a surgical instrument to a navigation array or other component. The coupling can reduce or eliminate movement between the instrument and the navigation array, improving navigation precision. The coupling can be quick and easy to use, reducing or eliminating the need for extra steps or additional tools to attach or detach the instrument from the coupling. In some embodiments, the single step of inserting an instrument into the coupling can automatically lock the instrument within the coupling in a toggle-free manner.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments.

Figure 1:
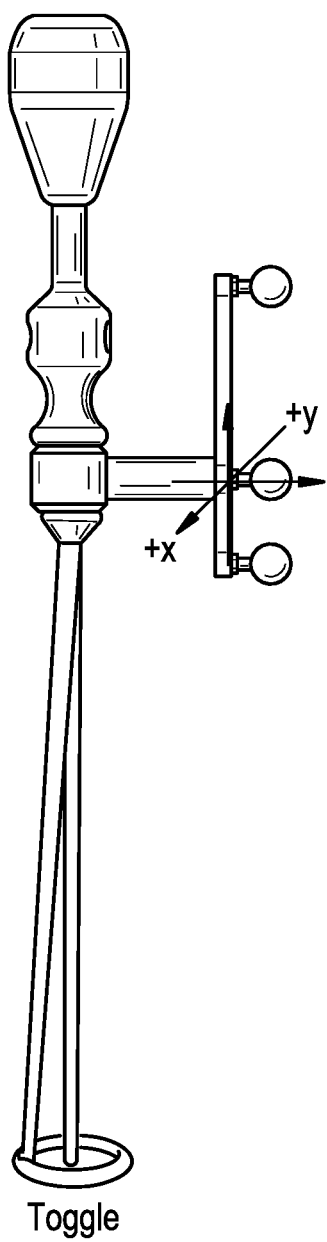
FIG. 1 is a perspective view of a prior art coupling, a navigation array, and an instrument.
Figure 2A:
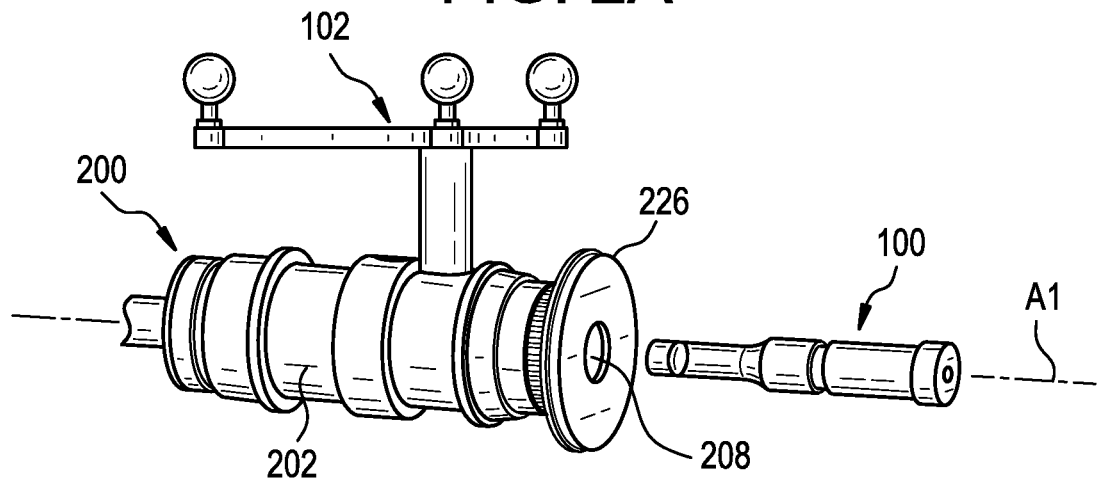
FIG. 2A is a perspective view of a coupling, a navigation array, and an instrument.
Figure 2B:
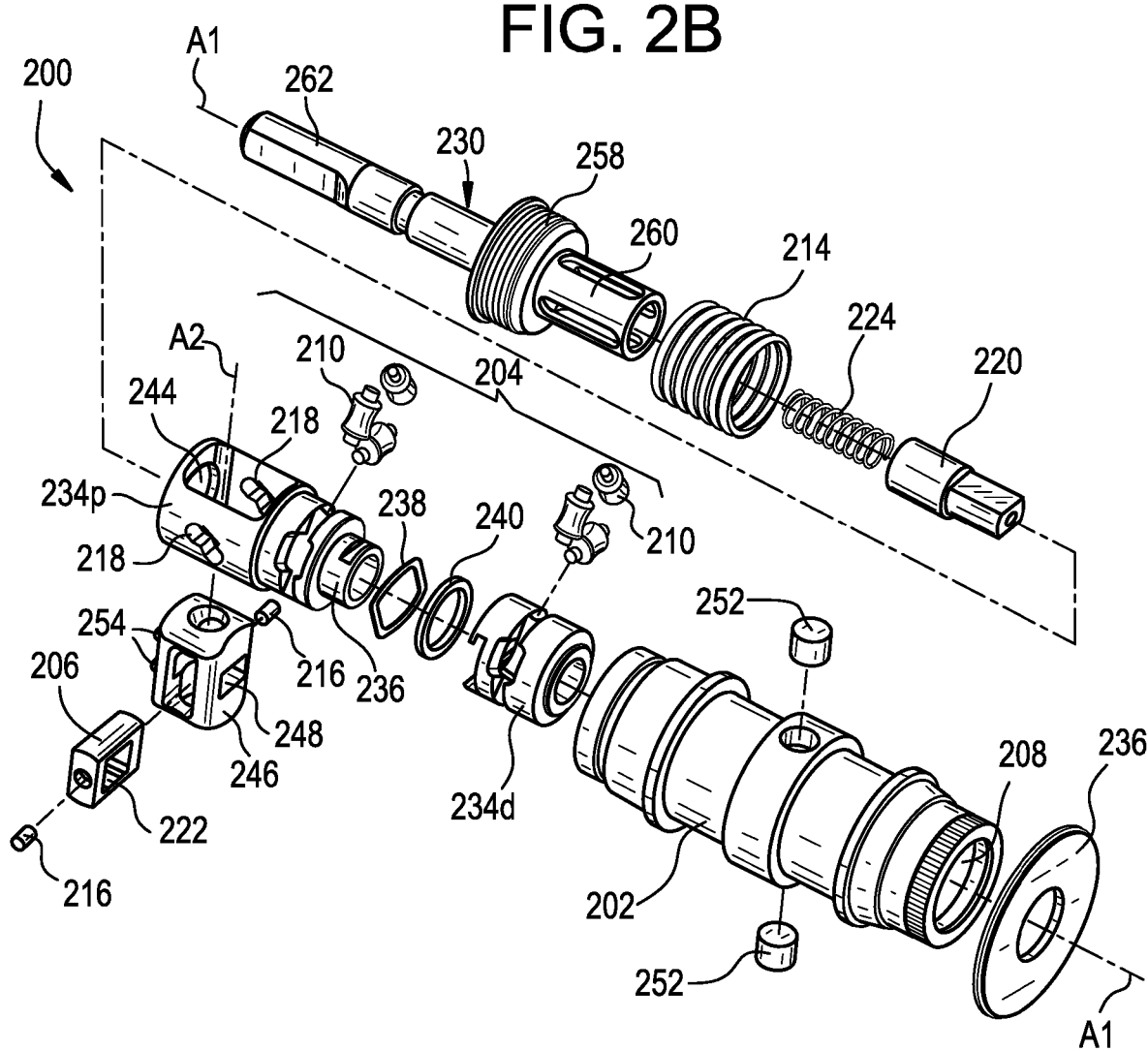
FIG. 2B is an exploded perspective view of the coupling of FIG. 2A.

FIGS. 2A-2P illustrate an exemplary embodiment of an instrument coupling 200. The coupling 200 can be used to attach an instrument 100 to another instrument, object, or component. For example, the coupling 200 can be used to attach an instrument 100 to a navigation array 102.

The coupling 200 can include a housing 202 in which a clamp 204 and a slider 206 are disposed. The coupling 200 can define a channel 208 configured to receive at least a portion of an instrument 100 therein.

The clamp 204 can be configured to translate longitudinally within the housing 202 along a central axis A1 of the housing. In a proximal position, one or more rollers, balls, or other clamping elements 210 of the clamp 204 can be free to move radially-outward, away from the central axis A1. In a distal position, ramped inner surfaces 212 of the housing 202 can bear against the clamping elements 210 to urge the clamping elements radially-inward towards the axis A1, thereby clamping onto an instrument 100 disposed in the channel 208. The clamp 204 can be biased towards the distal position by a clamp spring 214.

The slider 206 can be configured to translate laterally within the housing 202 along an axis A2 that is perpendicular to the central axis A1. In a first position, the slider 206 can interact with the clamp 204 via a slider pin 216 and a slope slot 218 to hold the clamp in the proximal, unclamped position. In a second position, the slider 206 can interact with the clamp 204 via the slider pin 216 and the slope slot 218 to allow the clamp to move towards the distal, clamped position under the bias of the clamp spring 214.

The coupling 200 can be movable between (i) an open position in which no instrument is received within the channel 208 and the coupling is prepared to receive an instrument, and (ii) a closed position in which an instrument is received within the channel and is securely engaged by the coupling to minimize or eliminate relative movement therebetween.

Figure 2C:
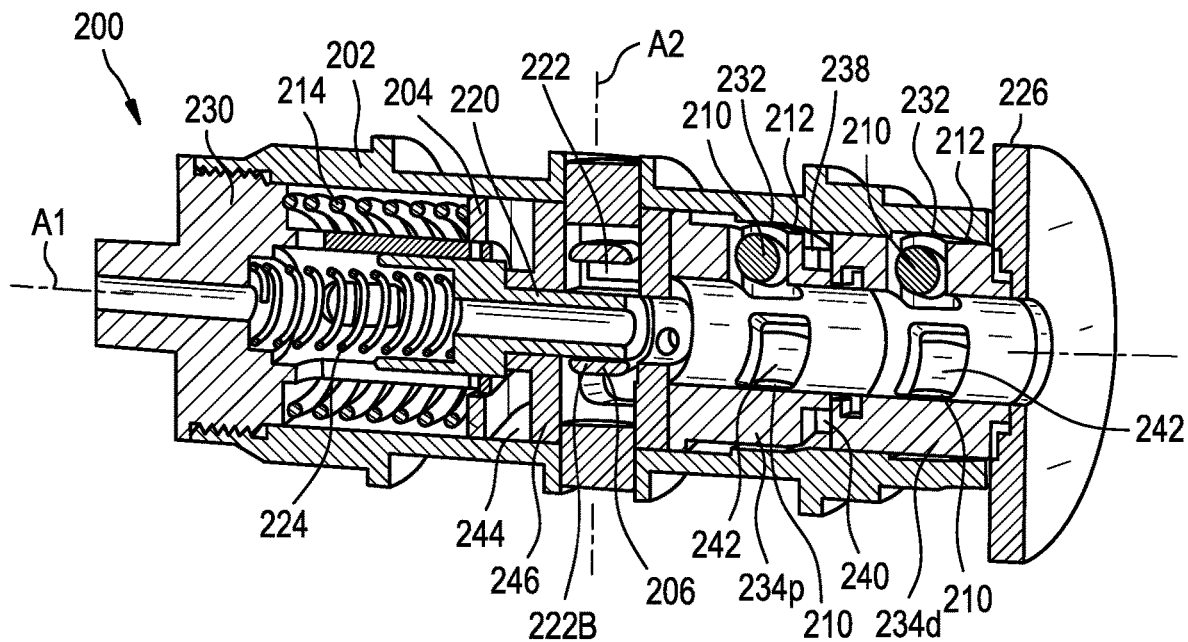
FIG. 2C is a sectional perspective view of the coupling of FIG. 2A in an open position.
Figure 2D:
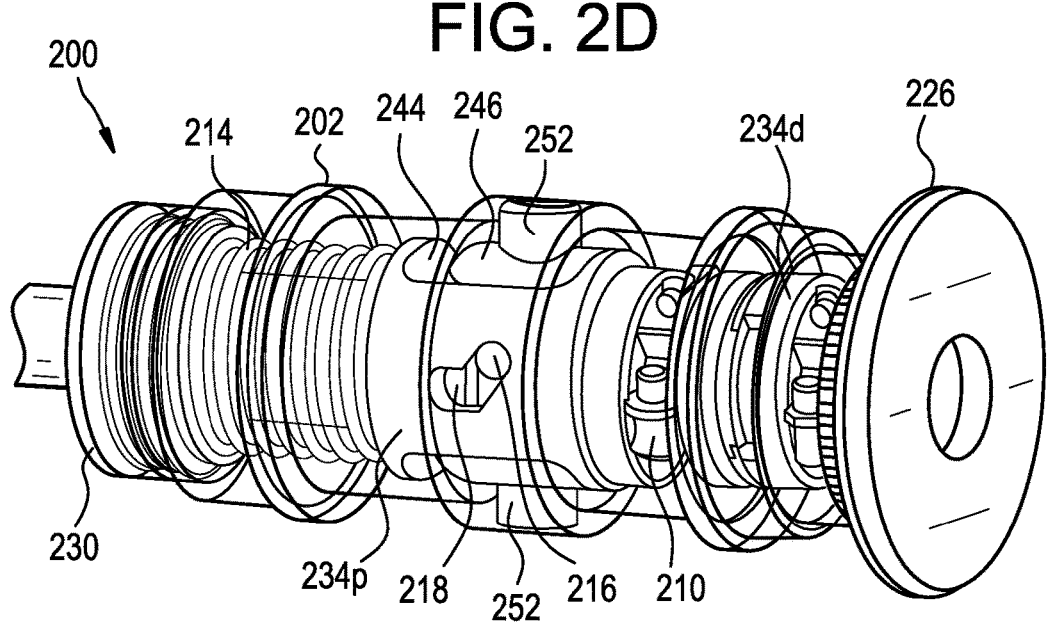
FIG. 2D is a perspective view of the coupling of FIG. 2A in an open position, with a housing of the coupling shown as transparent.

In the open position, as shown for example in FIGS. 2C-2D, an ejector 220 can be positioned within an opening 222 of the slider 206 to hold the slider in the first position described above, thereby holding the clamp 204 in the proximal, unclamped position.

Figure 2E:
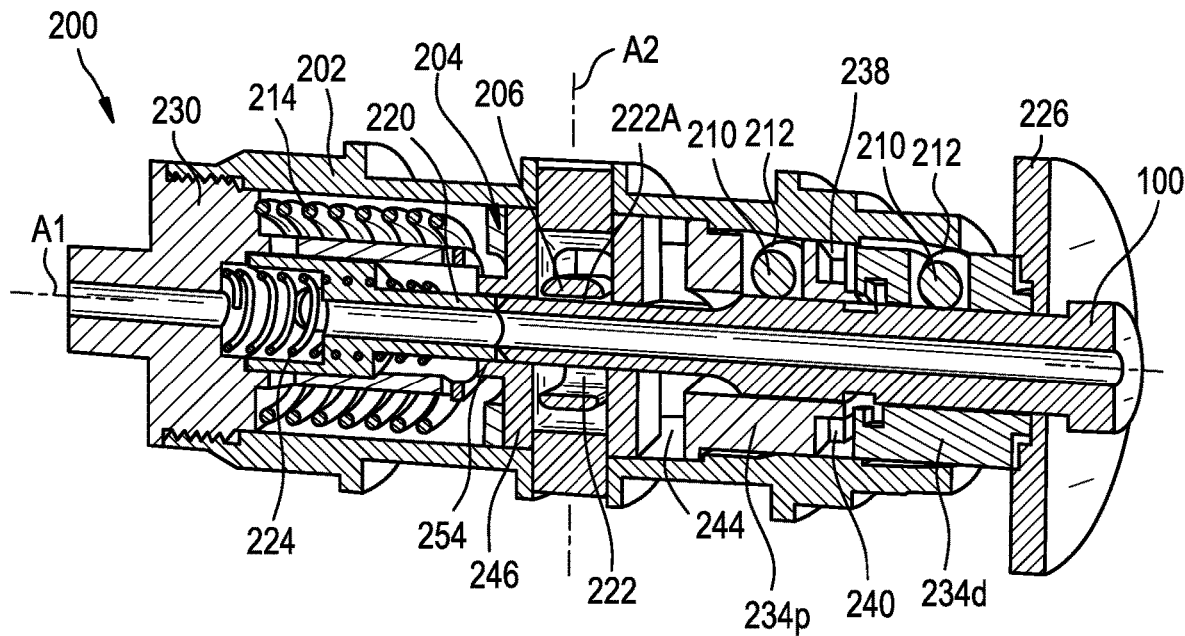
FIG. 2E is a sectional perspective view of the coupling of FIG. 2A in a closed position.
Figure 2F:
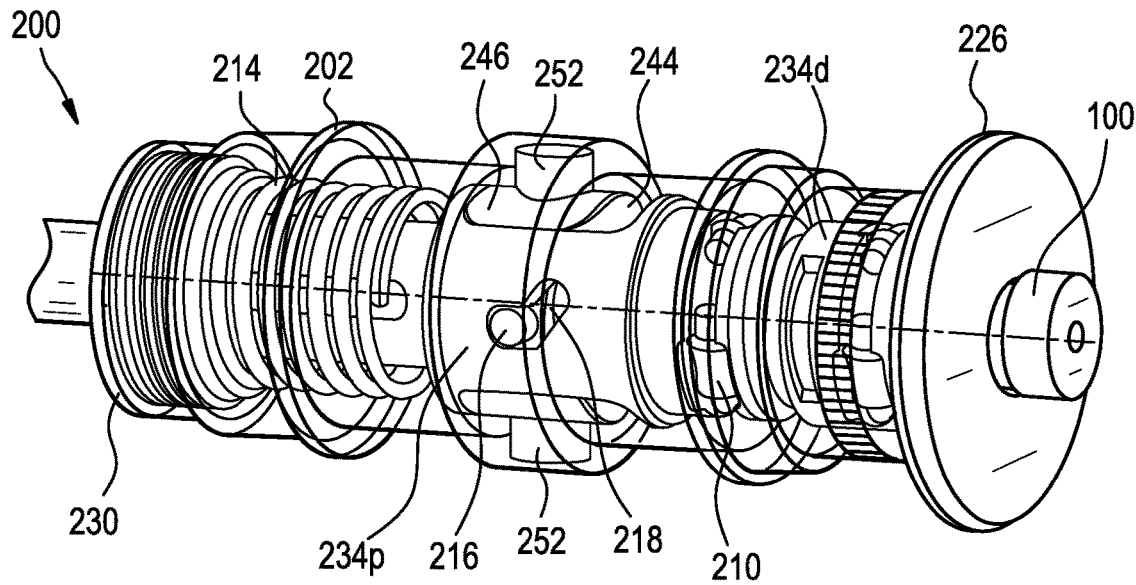
FIG. 2F is a perspective view of the coupling of FIG. 2A in a closed position, with a housing of the coupling shown as transparent.

In the closed position, as shown for example in FIGS. 2E-2F, insertion of an instrument 100 into the channel 208 can displace the ejector 220 proximally against the bias of an ejector spring 224. When the ejector 220 is moved out of the slider 206, the slider can be free to move to the second position described above, thereby releasing the clamp 204 to move to the distal, clamped position.

To release the instrument 100 and return the coupling 200 to the open position, a release plate 226 can be pushed proximally, e.g., by manual user input. Proximal movement of the release plate 226 can compress the clamp spring 214 and move the clamp 204 to the proximal, unclamped position. This movement of the clamp 204 can also move the slider 206 back to the first position, allowing the ejector 220 to move back into the opening 222 of the slider, pushing the instrument 100 out of the coupling 200 and once again holding the coupling in the open position.

The coupling 200 can thus allow for quick and toggle-free connection to an instrument. In some embodiments, the single step of pushing the instrument into the coupling can automatically lock the instrument to the coupling in a toggle-free manner, without requiring any additional steps or additional tools. Similarly, in some embodiments, the instrument can be released and the coupling reset in a single step, without requiring any additional steps or additional tools.

Figure 2G:
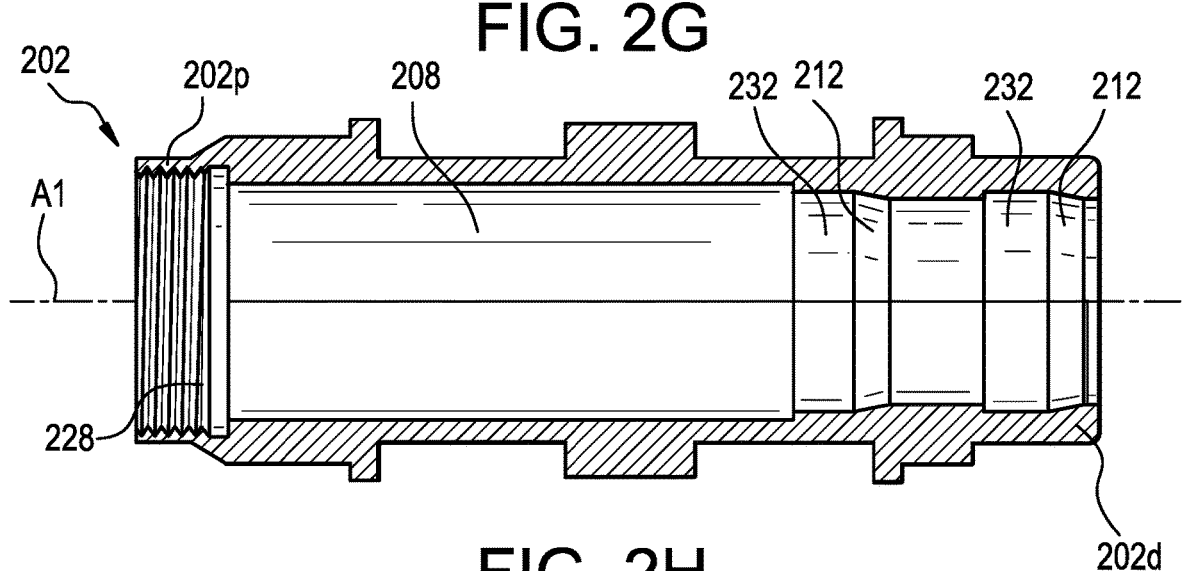
FIG. 2G is a sectional side view of the housing of the coupling of FIG. 2A.
Figure 2H:
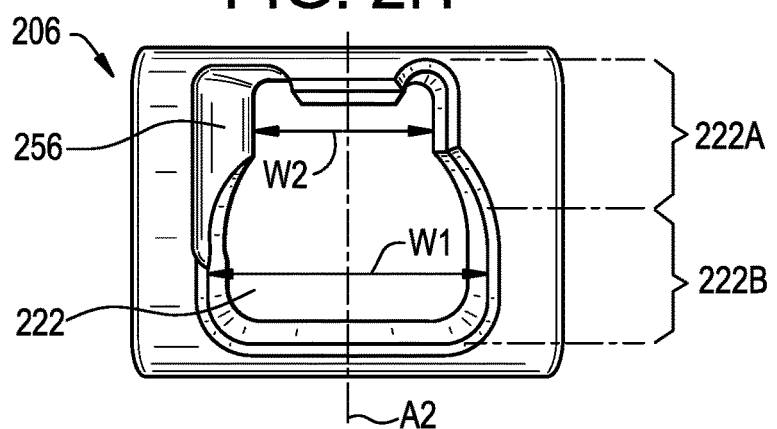
FIG. 2H is an end view of a slider of the coupling of FIG. 2A.
Figure 2I:
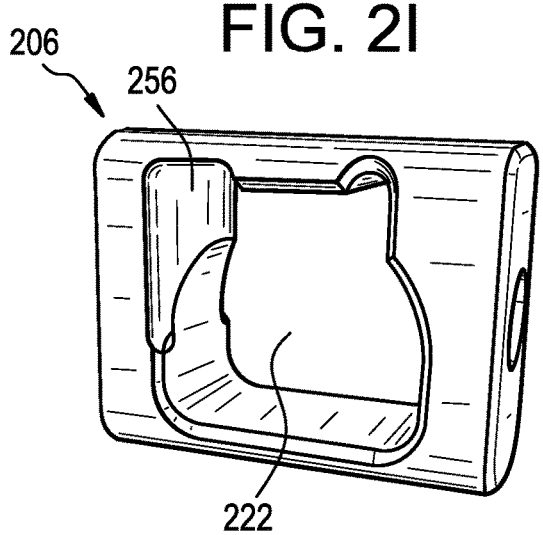
FIG. 2I is a perspective view of the slider of FIG. 2H from a distal vantage point.
Figure 2J:
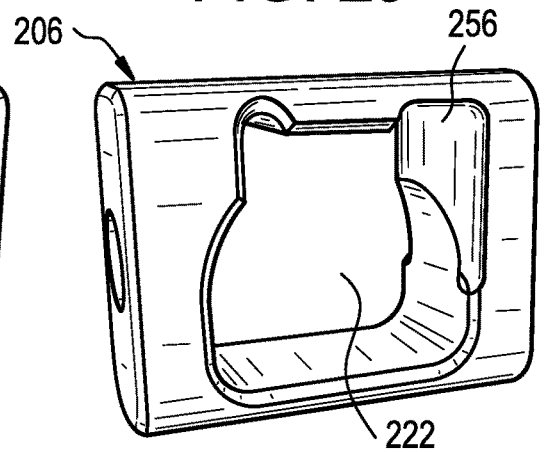
FIG. 2J is a perspective view of the slider of FIG. 2H from a proximal vantage point.
Figure 2Q:
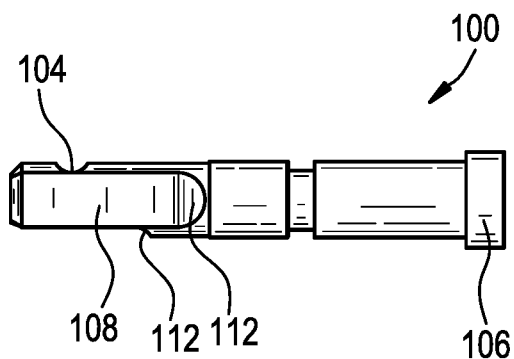
FIG. 2Q is a top view of an instrument that can be used with the coupling of FIG. 2A.
Figure 2R:
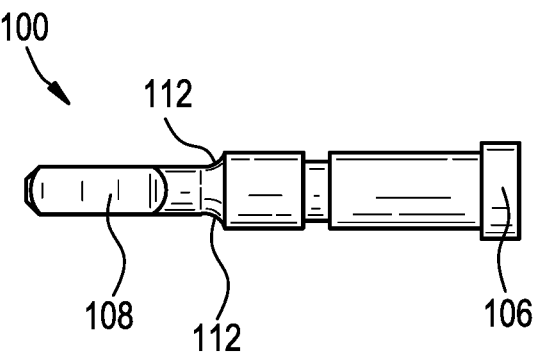
FIG. 2R is a side view of the instrument of FIG. 2Q.
Figure 2S:
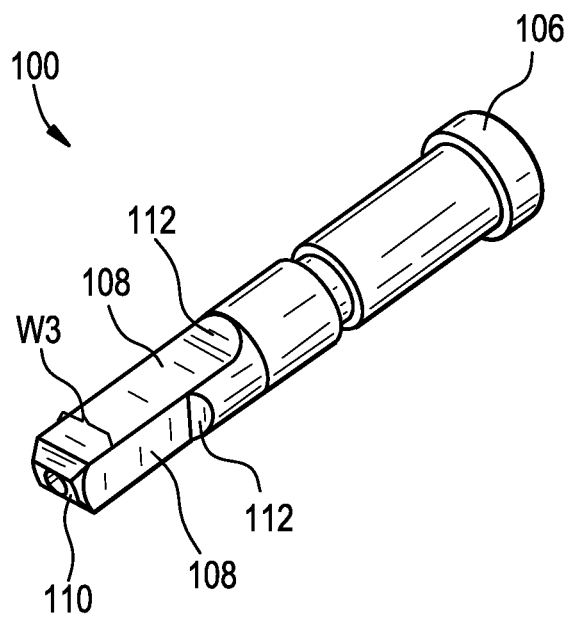
FIG. 2S is a perspective view of the instrument of FIG. 2Q.
Figure 2T:
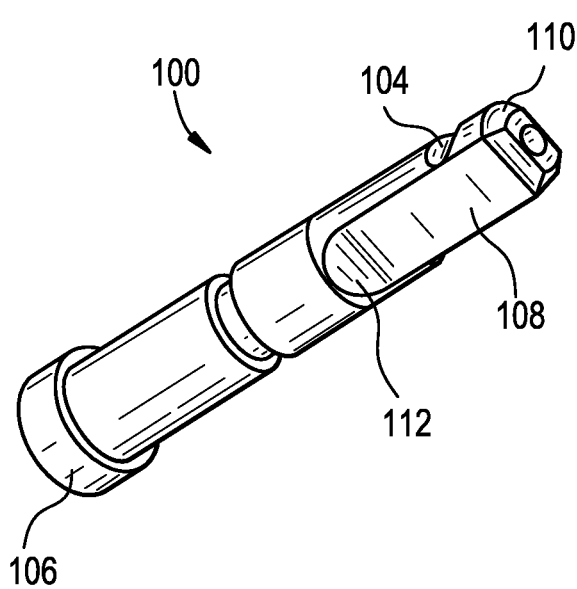
FIG. 2T is another perspective view of the instrument of FIG. 2Q.
Figure 2U:
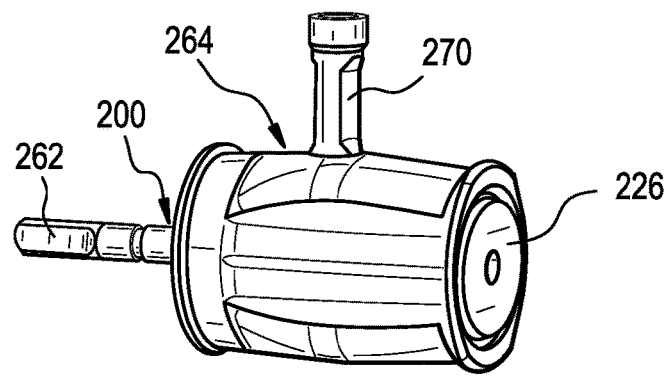
FIG. 2U is a perspective view of the coupling of FIG. 2A and a handle assembly.
Figure 2V:
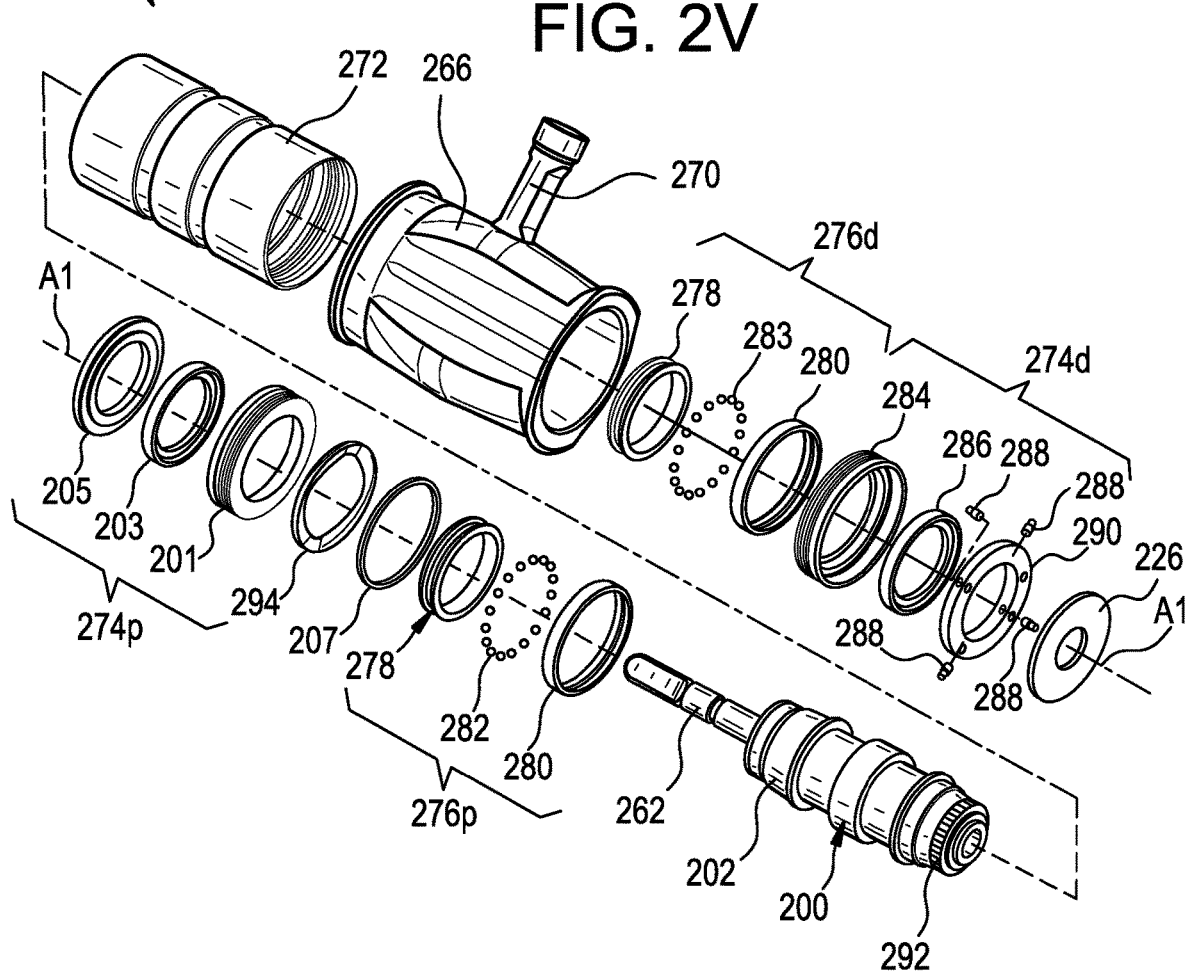
FIG. 2V is an exploded perspective view of the handle assembly and coupling of FIG. 2U.
Figure 2W:
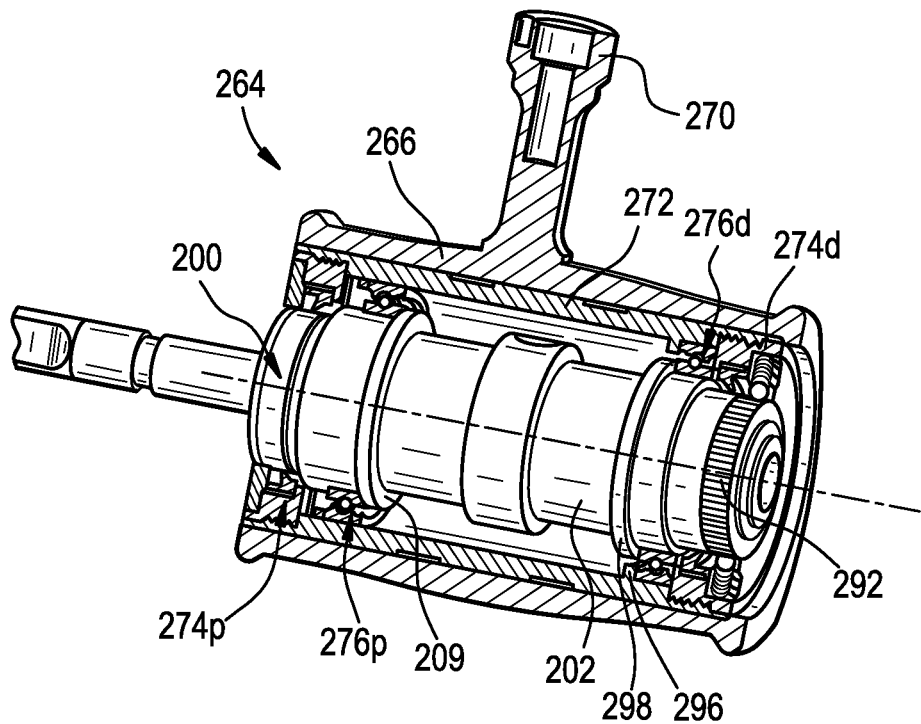
FIG. 2W is a sectional perspective view of the handle assembly and coupling of FIG. 2U.
Figure 2X:
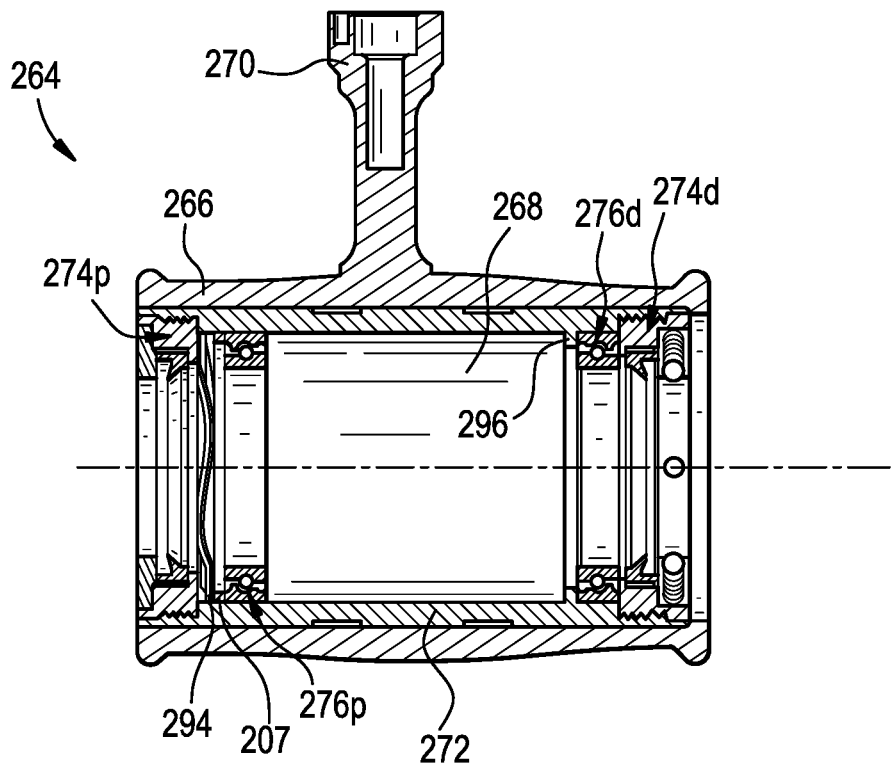
FIG. 2X is a sectional side view of the handle assembly of FIG. 2U.

As shown in FIG. 2G, the housing 202 can include a generally tubular body having proximal and distal ends 202p, 202d and a central longitudinal axis A1. The body of the housing 202 can define a central lumen or cavity 208 that extends between the proximal and distal ends 202p, 202d. The proximal end 202p of the housing 202 can include a mating feature, e.g., a threaded female recess 228 as shown, for attaching an end cap 230 to the housing. The navigation array 102 can be integrally formed with the housing 202 or can be attached thereto via various attachment mechanisms, such as a threaded, welded, snap-fit, interference, or other connection. As discussed further below with respect to FIGS. 2U-2X, the navigation array 102 can be coupled to a handle assembly 264 in which the housing 202 is rotatably mounted. The exterior surface of the housing 202 can include ribs, flanges, shoulders, or various other features for aligning, retaining, or otherwise interacting with such a handle assembly, as described in detail below.

The interior surface of the housing 202 can include surface features 212 for urging the clamping elements 210 of the clamp 204 radially-inward when the clamp translates longitudinally within the housing. In the illustrated embodiment, the interior surface of the housing 202 includes first and second conically-tapered sections 212. Each conical section 212 can be disposed adjacent to a cylindrical section 232. The cylindrical sections 232 can have a diameter equal to or greater than the base diameter of the conical sections 212. Accordingly, when longitudinally-aligned with the cylindrical sections 232, the clamping elements 210 can be free to move radially-outward, e.g., to disengage from an instrument 100. When longitudinally-aligned with the conical sections 212, the clamping elements 210 can be urged radially-inward, e.g., to engage an instrument 100. While two conical sections 212 are shown, it will be appreciated that the housing 202 can include any number of surface features, and that the surface features can instead be curved, stepped, or otherwise arranged to urge the clamping elements 210 inward as they are carried across the surface features. The illustrated surface features 212 extend around the entire inner circumference of the housing 202, though in other arrangements the surface features can be formed only in discrete positions about the circumference, which positions are aligned with the clamping elements 210. The surface features 212 can be formed in an integral sidewall of the housing 202 as shown, or in an insert disposed within the housing.

Referring again to FIGS. 2B-2F, the clamp 204 can include a cage 234 in which one or more clamping elements 210 are mounted. The illustrated cage 234 includes separate proximal and distal cage segments 234p, 234d, though in other arrangements a unitary cage can be used or a cage with more than two segments can be used. The proximal and distal segments 234p, 234d can include counterpart mating features for limiting relative longitudinal and/or rotational movement between the segments. For example, the proximal segment 234p can include a distally-projecting boss 236 with opposed rectangular cut-outs formed in an exterior surface thereof. The boss 236 can be received within a corresponding opening formed in the proximal end of the distal segment 234d, and the distal segment can include opposed tabs received within the cut-outs of the boss. The longitudinal dimension of the tabs can be less than a corresponding longitudinal dimension of the cut-outs, such that a small amount of relative longitudinal travel is permitted between the proximal and distal segments 234p, 234d.

A bias element 238 can be disposed between the proximal and distal cage segments 234p, 234d to bias the cage segments away from one another along the axis A1. For example, a wave spring 238 can be disposed between a distal-facing surface of the proximal segment 234p and a proximal-facing surface of the distal segment 234d, or of a washer 240 disposed between the segments. While a wave spring 238 is shown, in other arrangements a coil spring, leaf spring, or other bias element can be used instead or in addition. The bias element 238 can thus urge the distal cage segment 234d distally away from the proximal cage segment 234p. This can help ensure that both the clamping elements 210 of the proximal cage segment 234p and the clamping elements 210 of the distal cage segment 234d are firmly engaged with an instrument 100 when an instrument is inserted into the clamp 204. For example, if component geometry or tolerances are such that the clamping elements 210 of the proximal cage segment 234p engage the instrument 100 first, distal advancement of the proximal cage segment could stop before the distal cage segment 234d is advanced far enough to fully engage its clamping elements with the instrument. The bias element 238 can allow the distal cage segment 234d to continue advancing in such situations, ensuring that the clamping elements 210 of the distal cage are fully engaged with the instrument 100. Similarly, if component geometry or tolerances are such that the clamping elements 210 of the distal cage segment 234d engage the instrument 100 first, distal advancement of the distal cage segment could stop before the proximal cage segment 234p is advanced far enough to fully engage its clamping elements with the instrument. The bias element 238 can allow the proximal cage segment 234p to continue advancing in such situations, with the bias force of the clamp spring 214 overcoming the bias force of the bias element, ensuring that the clamping elements 210 of the proximal cage 234p are fully engaged with the instrument 100.

The clamp 204 can include one or more clamping elements 210 configured to move radially-inward or radially-outward in response to longitudinal movement of the clamp within the housing 202. For example, the clamp 204 can include a plurality of rollers 210 mounted to the clamp cage 234. The rollers 210 can be positioned in recesses formed in an exterior surface of the cage 234. At least a portion of the recesses can extend completely through the sidewall of the cage 234, such that at least a portion of a roller 210 positioned in the recess can move through the sidewall to engage an instrument 100 inserted through the cage. Opposed ends of the recess can form tracks in which an axle of the roller 210 is received to allow the roller to rotate about its central longitudinal axis within the recess. Each roller 210 can include a bearing surface 242 configured to contact and bear against an instrument 100 inserted through the cage 234. For example, the rollers 210 can each include a concave bearing surface 242. The concave bearing surface 242 can have a radius of curvature that is equal or substantially equal to an exterior radius of an instrument 100 with which the coupling 200 is to be used. While axle-mounted rollers 210 are shown, it will be appreciated that any of a variety of clamping elements can be used instead or in addition, such as wedges, balls, chucks, spring fingers, fins, and so forth.

In the illustrated clamp 204, the proximal and distal clamp segments 234p, 234d each include three rollers 210 spaced equally about the circumference of the clamp. In other arrangements, the clamp 204 can include a greater or lesser number of rollers 210, and/or rollers spaced in other positions.

The clamp 204 can be mechanically-linked to the slider 206, e.g., such that movement of the slider results in movement of the clamp and vice versa. The clamp 204 can include a cavity 244 in which the slider 206 is movably disposed. The illustrated cavity 244 is formed in the proximal clamp segment 234p, though in other arrangements the cavity can instead be formed in the distal clamp segment 234d. The longitudinal dimension of the cavity 244 can be greater than a corresponding longitudinal dimension of the slider 206, and/or a corresponding longitudinal dimension of a slider cage 246 in which the slider is mounted, such that the clamp 204 can translate longitudinally relative to the housing 202 while the slider remains at a fixed or substantially fixed longitudinal position relative to the housing. The cavity 244 can include opposed lateral sidewalls. One or both of the sidewalls can include an opening or slot 218 in which a slider pin 216 projecting outward from the slider 206 can be received. At least a portion of the slot 218 can be sloped such that, when the slider pin 216 is received in the sloped portion of the slot, translation of the slider 206 along the axis A2 causes translation of the clamp 204 along the axis A1 and vice versa. The sloped portion of the slot 218 can extend at an oblique angle with respect to the axis A1 and at an oblique angle with respect to the axis A2. The slot 218 can include a non-sloped portion. The non-sloped portion of the slot 218 can extend parallel to the axis A1 and perpendicular to the axis A2. When the slider pin 216 is disposed in the non-sloped portion of the slot 218, the clamp 204 can move longitudinally along the axis A1 (at least to the extent permitted by the length of the slot) without moving the slider 206 along the axis A2. The slot 218 can include a single sloped portion or a plurality of sloped portions. The slot 218 can include a single non-sloped portion or a plurality of non-sloped portions.

A release plate 226 can be coupled to a distal end of the clamp 204. For example, the release plate 226 can be press-fit, welded, or otherwise attached to a distal end of the distal clamp segment 234d. While a flat, disc-shaped release plate 226 is shown, it will be appreciated that the release plate can have any of a variety of shapes that facilitate application of a longitudinal force thereto by a user. In use, as described further below, the release plate 226 can be urged proximally relative to the housing 202 to push the clamp 204 proximally and release the clamping elements 210 from an instrument 100 received within the coupling 200 to detach the instrument from the coupling.

The slider 206 can be mounted within a slider cage 246 disposed in the cavity 244 of the clamp 204. The slider cage 246 can include a longitudinal throughbore 248 sized to receive an instrument 100 and/or the ejector 220 therethrough. The slider cage 246 can include a transverse throughbore 250 sized to receive the slider 206 therethrough. The transverse throughbore 250 can have a height along the axis A2 that is greater than a height of the slider 206 along the axis A2, such that the slider can translate within the transverse throughbore along the axis A2. The slider cage 246 can include opposed planar sidewalls that engage corresponding planar sidewalls of the clamp cavity 244 to prevent rotation of the clamp 204 relative to the slider cage about the axis A1. The slider cage 246 can include opposed cylindrical sidewalls that engage the interior surface of the housing 202. The opposed cylindrical sidewalls can be pinned to the housing 202 via one or more mating pins 252 to prevent rotation of the slider cage 246, and by extension the clamp 204, relative to the housing about the axis A1. The mating pins 252 can also secure the slider cage 246 and the slider 206 at a fixed or substantially fixed longitudinal position within the housing 202. The slider cage 246 can include one or more proximally-extending projections 254 that engage the ejector 220 to prevent rotation of the ejector relative to the slider cage and the housing 202 about the axis A1, even when the ejector is displaced proximally out of the slider 206.

The slider 206 is shown in greater detail in FIGS. 2H-2P. The slider 206 can include a generally rectangular parallelepiped body. The slider 206 can include a cut-out or opening 222 extending longitudinally through the body along the axis A1 and sized to receive at least a portion of an instrument 100 and/or the ejector 220 therethrough. The slider 206 can include an engagement feature 256 for engaging with an instrument 100 in certain positions of the slider to help secure the instrument within the coupling 200. For example, a sidewall of the opening 222 can define a protrusion 256 sized to be received within a corresponding depression or recess 104 of an instrument 100. Engagement between the protrusion 256 and the depression 104 can be effective to lock an axial position of the instrument 100 with respect to the slider 206 and the coupling 200. The proximal-facing surface of the protrusion 256 and/or the distal-facing surface of the protrusion can be curved, ramped, or otherwise tapered. For example, the protrusion 256 can be formed as a section of a cylinder extending parallel to the axis A2 as shown. Such features can interact with corresponding surface geometry of the instrument depression 104 to center the protrusion 256 within the recess and/or to push or pull the instrument 100 to a predetermined longitudinal position relative to the coupling 200.

The slider opening 222 can include an upper portion 222A and a lower portion 222B. The lower portion 222B of the opening 222 can have a width W1 perpendicular to the axis A2 that is greater than or equal to a corresponding width of the ejector 220. Accordingly, the ejector 220 can be free to slide longitudinally into and out of the lower portion 222B of the opening 222, as shown for example in FIG. 2O. The upper portion 222A of the opening 222 can have a width W2 perpendicular to the axis A2 that is less than a corresponding width of the ejector 220. Accordingly, the ejector 220 cannot fit within the upper portion 222A of the opening 222 and, when the ejector is positioned in the lower portion 222B of the opening, translation of the slider 206 along the axis A2 is prevented by interference between the ejector and the sidewalls of the upper portion of the opening.

As described further below, an instrument 100 with which the coupling 200 is to be used can have a mating geometry with a width W3 perpendicular to the axis A2 that is less than or equal to the width W2 of the upper portion 222A of the opening 222. Accordingly, the mating geometry of the instrument 100 can fit within the upper portion 222A of the opening 222 and the sidewalls of the upper portion of the opening do not interfere with translation of the slider 206 along the axis A2 when the mating geometry of the instrument is inserted through the slider, as shown for example in FIG. 2P.

The slider 206 can include one or more slider pins or other protrusions that project outward from the slider. For example, the slider 206 can include first and second slider pins 216 that extend from opposed sidewalls of the slider and that are received within respective ones of the slots 218 formed in the clamp 204.

The slider 206 can be translated along the axis A2 to position the slider with respect to the coupling 200 in at least a first position and a second position. In the first position, as shown for example in FIGS. 2K, 2M, and 2O, the lower portion 222B of the slider opening 222 can be aligned with the longitudinal throughbore 248 of the slider cage 246. In the second position, as shown for example in FIGS. 2L, 2N, and 2P, the upper portion 222A of the slider opening 222 can be aligned with the longitudinal throughbore 248 of the slider cage 246.

Referring again to FIGS. 2B-2F, the end cap 230 can close the proximal end of the housing 202. The end cap 230 can include a mating feature, e.g., a male threaded plug 258 as shown, for attaching the end cap to the proximal end of the housing 202. The end cap 230 can include a distally-extending boss 260 in which the ejector spring 224 can be received and in which a proximal portion of the ejector 220 can be slideably mounted. The boss 260 can include sidewall openings, e.g., to facilitate cleaning and/or sterilization of the coupling 200. The end cap 230 can define one or more distal-facing spring seats. For example, the clamp spring 214 can be disposed between a distal-facing surface of the end cap 230 and a proximal-facing surface of the clamp 204, such that the clamp is biased distally away from the end cap. As another example, the ejector spring 224 can be disposed between a distal-facing surface of the end cap 230 and a proximal-facing surface of the ejector 220, such that the ejector is biased distally away from the end cap. The ejector spring 224 and the clamp spring 214 can be coaxial as shown. While coil springs are shown for the ejector spring 224 and the clamp spring 214, alternative bias elements can be used for one or both springs, such as wave springs, leaf springs, and the like.

The end cap 230 can include a mating geometry 262 extending proximally therefrom. The mating geometry 262 of the end cap 230 can be the same as the mating geometry of an instrument 100 with which the coupling 200 is to be used, or can differ in one or more respects. The mating geometry 262 can include one or more flats, e.g., to facilitate torque application to the coupling 200 and an instrument 100 received therein about the axis A1. The mating geometry 262 can allow the coupling 200 to be connected to various other instruments or components, such as a drill, a driver, a knob or handle, a navigation array, and so forth. The mating geometry 262, the end cap 230, and/or the ejector 220 can be cannulated. The cannulation can be configured to align with a corresponding cannulation of an instrument 100 when the instrument is received within the coupling 200. The cannulation can allow the coupling 200 and an instrument 100 received therein to be inserted over a guidewire, or can allow cement or other flowable material to be delivered through the coupling and an instrument received therein.

The ejector 220 can be defined by a generally cylindrical plunger body. A proximal portion of the ejector 220 can be slidably mounted in the boss 260 of the end cap 230, and can be biased distally by the ejector spring 224. A distal portion of the ejector 220 can include one or more flats, which can engage with the lower portion 222B of the slider opening 222 or the proximal extensions 254 of the slider cage 246 to prevent rotation of the ejector about the axis A1.

An exemplary instrument mating geometry is shown in FIGS. 2Q-2T. It will be appreciated that the illustrated geometry is exemplary and that the coupling 200 can be used with any of a variety of instruments having any of a variety of mating geometries. In some embodiments, the mating geometry of the instrument can be a cylindrical shaft. In some embodiments, the mating geometry of the instrument can be a cylindrical shaft with one or more flats formed therein.

As shown in FIGS. 2Q-2T, the instrument 100 can include a generally cylindrical shaft 106 with a mating geometry at or near the proximal end of the shaft. The distal end of the shaft (not shown) can include the functional operating features of the instrument 100, such as an end effector, blade, rasp, tap, drill, etc. The instrument shaft 106 can be cannulated, e.g., to allow the instrument 100 to be inserted over a guidewire or to allow cement or other flowable materials to be delivered through the instrument.

The mating geometry can include a section of the instrument shaft 106 with one or more flats 108. For example, the mating geometry can include a section of the instrument shaft 106 having a rectangular or substantially rectangular transverse cross-section. The flats 108 of the mating geometry can interact with the slider 206 to limit or prevent rotation of the instrument shaft 106 relative to the coupling 200 about the axis A1. This can allow, in some instances, for torque about the axis A1 applied to the coupling 200 to be transferred to the instrument 100 and vice versa.

The mating geometry can include at least one depression or recess 104 configured to engage with the protrusion 256 of the slider 206, as described above. The depression 104 can interact with the slider 206 to limit or prevent axial translation of the instrument 100 relative to the coupling 200 along the axis A1. The depression 104 can be formed in the same portion of the instrument shaft in which the one or more flats 108 are formed.

The mating geometry can include a bulleted or tapered proximal-most tip 110. The mating geometry can include ramped, curved, or otherwise tapered transitions 112 from the one or more flats 108 to the cylindrical outside diameter of the instrument shaft. Such features can act as lead-in surfaces, urging the clamping elements 210 of the coupling 200 radially-outward as the instrument 100 is initially inserted into the coupling. One or more of the transitions 112 can be longitudinally-offset from each other along the length of the instrument 100. As noted above, the outside radius of the portion of the instrument shaft received within the clamp 204 can be equal or substantially equal to the radius of the concave bearing surfaces 242 of the clamping elements 210.

The mating geometry can be keyed such that the instrument 100 can only be inserted into the coupling 200, and in particular into the slider opening 222, in one orientation or in a limited number of orientations. This can help ensure that the depression 104 of the instrument 100 is aligned with the protrusion 256 of the slider opening 222. This can also help ensure that the navigation array 102 is coupled to the instrument 100 in a predetermined or known orientation, which may be necessary when navigating an asymmetrical instrument. A keyed interface between the mating geometry and the coupling 200 can also prevent use of the coupling with unauthorized or unintended instruments.

As noted above, the mating geometry can include a section of the instrument shaft having a width W3 that is less than or equal to the width W2 of the upper portion 222A of the slider opening 222. This can allow the mating geometry of the instrument 100 to fit within the upper portion 222A of the slider opening 222, allowing the slider 206 to translate along the axis A2 when the instrument is inserted therethrough.

In use, the coupling 200 can be used to attach an instrument 100 to another instrument, object, or component. For example, the coupling 200 can be used to attach an instrument 100 to a navigation array 102.

The coupling 200 can be movable between (i) an open position in which no instrument is received within the channel 208 and the coupling is prepared to receive an instrument, and (ii) a closed position in which an instrument is received within the channel and is securely engaged by the coupling to minimize or eliminate relative movement therebetween.

FIGS. 2C-2D illustrate the coupling 200 in the open position. As shown, the ejector 220 can be positioned within the lower portion 222B of the slider opening 222, preventing translation of the slider 206 along the axis A2 and holding the slider in a first position. The ejector 220 can be maintained within the slider 206 by the bias of the ejector spring 224 urging the ejector distally away from the end cap 230. With the slider 206 in the first position, each slider pin 216 can be positioned at the upper end of the sloped portion of its respective clamp slot 218. Because the slider 206 is prevented by the ejector 220 from translating along the axis A2, the slider pins 216 cannot travel within the clamp slots 218 and therefore the slider pins hold the clamp 204 in a proximal, unclamped position. In particular, in the proximal, unclamped position of the clamp 204, the clamping elements 210 can be aligned with the relief portions 232 of the inner surface of the housing 202, such that the clamping elements are free to move radially-outward away from the axis A1. In the proximal, unclamped position, the clamp spring 214 can be compressed between the clamp 204 and the end cap 230. FIGS. 2K and 2M illustrate the slider 206 and the slider housing 246 when the coupling 200 is in the open position. FIG. 2O is a sectional view of the coupling 200 in the open position, illustrating the ejector 220 inserted through the slider opening 222.

FIGS. 2E-2F illustrate the coupling 200 in the closed position. As shown, insertion of an instrument 100 into the channel 208 can displace the ejector 220 proximally, compressing the ejector spring 224 and moving the ejector out of the slider opening 222. When the ejector 220 is moved out of the slider opening 222, the slider 206 can be free to translate along the axis A2 and out of the first position. With the slider 206 no longer being held in the first position, the slider pins 216 can be free to travel within the clamp slots 218 and therefore the clamp 204 is released to translate longitudinally within the housing 202. The bias force supplied by the clamp spring 214 can urge the clamp 204 distally, thereby guiding the clamping elements 210 along the ramped bearing surfaces 212 of the housing 202 to move the clamping elements radially inward into firm engagement with the instrument 100. As the clamp 204 moves distally under the force of the clamp spring 214, the slider pins 216 can travel along the sloped portions of the clamp slots 218, urging the slider 206 into a second position in which the upper portion 222A of the slider opening 222 is aligned with the longitudinal throughbore 248 of the slider cage 246. In the second position, the protrusion 256 of the slider opening 222 can be received within a corresponding depression 104 of the instrument 100. FIGS. 2L and 2N illustrate the slider 206 and the slider housing 246 when the coupling 200 is in the closed position. FIG. 2P is a sectional view of the coupling 200 in the closed position, illustrating the instrument 100 inserted through the slider opening 222.

Once the slider 206 is in the second position, the slider pins 216 can travel along the non-sloped portions of the clamp slots 218 to allow the clamp 204 to continue advancing distally to the extent needed to clamp the instrument 100. The proximal and distal cage segments 234p, 234d of the clamp 204 can advance distally to the same or to different degrees, as described above. For example, the proximal cage segment 234p can translate distally along the axis A1 until the clamping elements 210 mounted thereto are firmly wedged between the ramped surface 212 of the housing 202 and the instrument 100. If the clamping elements 210 of the distal cage segment 234d are not yet firmly wedged between the ramped surface 212 of the housing 202 and the instrument 100, the distal segment can continue to advance under the force of the bias element 238 until such wedging occurs. Similarly, the distal cage segment 234d can translate distally along the axis A1 until the clamping elements 210 mounted thereto are firmly wedged between the ramped surface 212 of the housing 202 and the instrument 100. If the clamping elements 210 of the proximal cage segment 234p are not yet firmly wedged between the ramped surface 212 of the housing 202 and the instrument 100, the proximal segment can continue to advance under the force of the clamp spring 214, compressing the bias element 238 until such wedging occurs.

In the closed position, the slider protrusion 256 can be received within the depression 104 of the instrument 100 to limit or prevent translation of the instrument along the axis A1 relative to the coupling 200, e.g., limiting or preventing surging movement, and/or to limit or prevent rotation of the instrument 100 about the axis A1 relative to the coupling 200, e.g., limiting or preventing roll movement. Also in the closed position, the clamping elements 210 can be wedged against the exterior surface of the instrument 100 to limit or prevent lateral translation of the instrument relative to the coupling 200, to limit or prevent translation of the instrument along the axis A1 relative to the coupling 200, to limit or prevent rotation of the instrument 100 about the axis A1 relative to the coupling 200, and/or to limit or prevent pivoting movement of the instrument relative to the coupling 200, e.g., limiting or preventing heaving, swaying, surging, rolling, pitching, and/or yawing movement. The coupling 200 can thus limit or prevent movement of the instrument 100 relative to the coupling in at least six degrees of freedom. It will be appreciated that, in some embodiments, the coupling 200 can be configured to preserve one or more of these degrees of freedom.

To release the instrument 100 and return the coupling 200 to the open position, the release plate 226 can be pushed proximally, e.g., by manual user input. Proximal movement of the release plate 226 can move the clamp 204 proximally relative to the housing 202 to the proximal, unclamped position, compressing the clamp spring 214. With the clamping elements 210 now offset from the ramped bearing surfaces 212 of the housing 202, the clamping elements can be free to move radially-outward to disengage from the instrument 100. As the clamp 204 moves proximally, the slider pins 216 can travel along the clamp slots 218, forcing the slider 206 to translate along the axis A2 to the first position. This movement of the slider 206 can remove the slider protrusion 256 from the depression 104 of the instrument 100, allowing the instrument to move axially relative to the coupling 200. This movement of the slider 206 can also align the lower portion 222B of the slider opening 222 with the longitudinal throughbore 248 of the slider cage 246. Accordingly, the ejector 220 can be again free to slide distally into the slider opening 222, under the bias force of the ejector spring 224. Distal movement of the ejector 220 can urge the instrument 100 distally out of the channel 208 of the coupling 200. When the user-applied force is removed from the release plate 226, the ejector 220 can remain within the slider 206, holding the coupling 200 in the open position described above such that the coupling is ready to be coupled to an instrument 100.

The coupling 200 can be used to attach an instrument 100 to another instrument, object, or component. For example, the coupling 200 can be used to attach an instrument 100 to a navigation array 102. The navigation array or other component can be attached directly to the outer housing 202 of the coupling 200, e.g., as shown in FIG. 2A, or can be coupled thereto via one or more intermediate components, e.g., a handle assembly of the type described below.

FIGS. 2U-2X illustrate an exemplary handle assembly 264 that can be used with the coupling 200. The coupling 200 can be mounted in the handle assembly 264 such that the coupling is selectively rotatable relative to the handle assembly about the axis A1. The handle assembly 264 can include an outer body 266 that defines a central channel 268 in which the coupling 200 can be mounted. The outer body can include a mating feature 270 for attaching the handle assembly 264 to a navigation array 102 or other component. Alternatively, or in addition, the navigation array or other component can be formed integrally with the outer body 266 or can be directly attached to the outer body, e.g., via welding, adhesives, or other attachment means.

The handle assembly 264 can include an insert 272 disposed within the central channel 268. Proximal and distal end caps 274p, 274d can close the respective ends of the channel 268. The coupling 200 can be rotatably supported within the channel 268 by one or more bearings. For example, as shown, the handle assembly 264 can include proximal and distal bearings 276p, 276d. The illustrated bearings 276p, 276d are race bearings each having an inner race 278, an outer race 280, and a set of ball bearings 282 captured therebetween. While race bearings are shown, any of a variety of other bearings can be used instead or in addition, such as fluid bearings and the like.

The distal end cap 274d can include a threaded plug 284 configured to be threaded into a distal recess of the insert 272. The threaded plug 284 can include a seal ring 286 with a flexible or semi-flexible lip that contacts and forms a seal with the outer surface of the coupling housing 202. The handle assembly 264 can also include a locking element. For example, the threaded plug 284 can include one or more ball plungers 288. The ball plungers 288 can be mounted in a ring insert 290 mounted in the distal end cap 274d. The illustrated end cap 274d includes four ball plungers 288 spaced equally about the circumference of the end cap, through it will be appreciated that the end cap can include any number of ball plungers at various positions. The ball plungers 288 can be biased radially-inward into engagement with a plurality of radial teeth 292 formed in the outer surface of the coupling 200.

The ball plungers 288 can hold the coupling 200 at a fixed rotational position about the axis A1 relative to the handle assembly 264, until sufficient torque is applied to overcome the spring force of the ball plungers. When this occurs, the ball plungers 288 can be compressed into the end cap 274d, allowing the coupling 200 to slip by one or more teeth 292 relative to the handle assembly 264.

Alternatively, or in addition, the rotational position of the coupling 200 relative to the handle assembly 264 can be adjusted by advancing the handle assembly distally relative to the coupling. This can move the ball plungers 288 out of engagement with the teeth 292 and thereby allow free rotation of the coupling 200 relative to the handle assembly 264. The handle assembly 264 can then be retracted proximally relative to the coupling 200, e.g., under the force of a bias element 294 as described further below, to once again engage the ball plungers 288 with the teeth 292 and lock rotation between the coupling and the handle assembly.

The ball plungers 288 can thus secure the coupling 200 in any of a plurality of discrete rotational positions about the axis A1 relative to the handle assembly 264. While ball plungers 288 are shown, it will be appreciated that various other mechanisms for selectively locking rotation can be used instead or in addition, such as spring fingers, a ratchet and pawl system, and so forth.

When the distal end cap 274d is threaded into the insert 272, the distal bearing 276d can be held in a fixed longitudinal position by the distal end cap and by a flange 296 that extends radially-inward from the insert. Distal travel of the coupling 200 relative to the insert 272 can be limited by interference between the distal bearing 276d and a flange 298 that extends radially-outward from the coupling 200.

The proximal end cap 274p can include a threaded plug 201 configured to be threaded into a proximal recess of the insert 272. The threaded plug 201 can include a seal ring 203 with a flexible or semi-flexible lip that contacts and forms a seal with the outer surface of the coupling housing 202. The threaded plug 201 can also include a proximal cover 205.

A bias element 294 can be positioned within the handle assembly 264 to bias the coupling 200 distally relative to the handle assembly. For example, as shown, a wave spring 294 can be disposed between the proximal end cap 274p and a washer 207 which is pressed by the wave spring against the proximal bearing 276p, which is in turn pressed by the wave spring against a flange 209 that extends radially-outward from the coupling housing 202. It will be appreciated that this arrangement is exemplary, and that other bias elements can be used instead or in addition and can be positioned at other locations within the handle assembly 264.

The bias element 294 can help return the handle assembly 264 proximally over the coupling 200 to re-engage the ball springs 288 with the coupling teeth 292 after a rotational adjustment is performed. The bias element 294 can be configured to take up any "slack" in the handle assembly 264, e.g., due to material expansion or contraction, manufacturing tolerances, or other factors, to ensure that the coupling 200 is positioned at a known or predetermined longitudinal location with the handle assembly. For example, the distally-directed bias force can help ensure that the coupling 200 is maintained at the distal-most limit of its travel within the handle assembly 264, as defined by engagement between the coupling flange 298, the distal bearing 276d, and the distal end cap 274d. Securing the coupling 200 at a known location within the handle assembly 264 can help avoid introduction of navigation error into the system.

The handle assembly 264 can thus be used to selectively adjust the rotational position of the navigation array 102 (or other attached component) relative to the coupling 200 about the axis A1. The adjustment can be performed quickly and easily by the user, for example by simply grasping the handle 264 and rotating it relative to the instrument 100 to overcome the spring force of the ball plungers 288. As another example, the user can grasp the handle 264, slide it distally relative to the instrument 100, rotate the handle to the desired position, and then release the handle to allow it to slide proximally and restore the rotation lock.

FIGS. 3A-3E illustrate an exemplary embodiment of an instrument coupling 300. The coupling 300 can be used to attach an instrument 100 to another instrument, object, or component. For example, the coupling 300 can be used to attach an instrument 100 to a navigation array 102. Except as described below and as will be readily appreciated by one having ordinary skill in the art in view of the present disclosure, the structure and operation of the coupling 300 is substantially the same as that of the coupling 200, and therefore a detailed description is omitted here for the sake of brevity.

For example, the coupling 300 can include an outer housing 302 with ramped inner surfaces 312 and a central axis A1, a clamp 304 with one or more clamping elements 310 mounted thereto and one or more slope slots 318, a slider 306 engaged with the one or more slope slots of the clamp and translatable along an axis A2, an ejector 320, an end cap 330, an ejector spring 324 that biases the ejector distally, a clamp spring 314 that biases the clamp distally, and a release plate 326, all being substantially of the type described above.

The coupling 300 can include a single clamp cage 334, as opposed to the multi-segment cage shown above. The coupling 300 can include a slider 306 mounted within the outer housing 302 of the coupling, instead of in a slider cage as shown above. The illustrated instrument 100 does not extend through the slider body 306, but instead an outer surface of the slider body engages the instrument depression 104 when in the closed position.

Figure 3A:
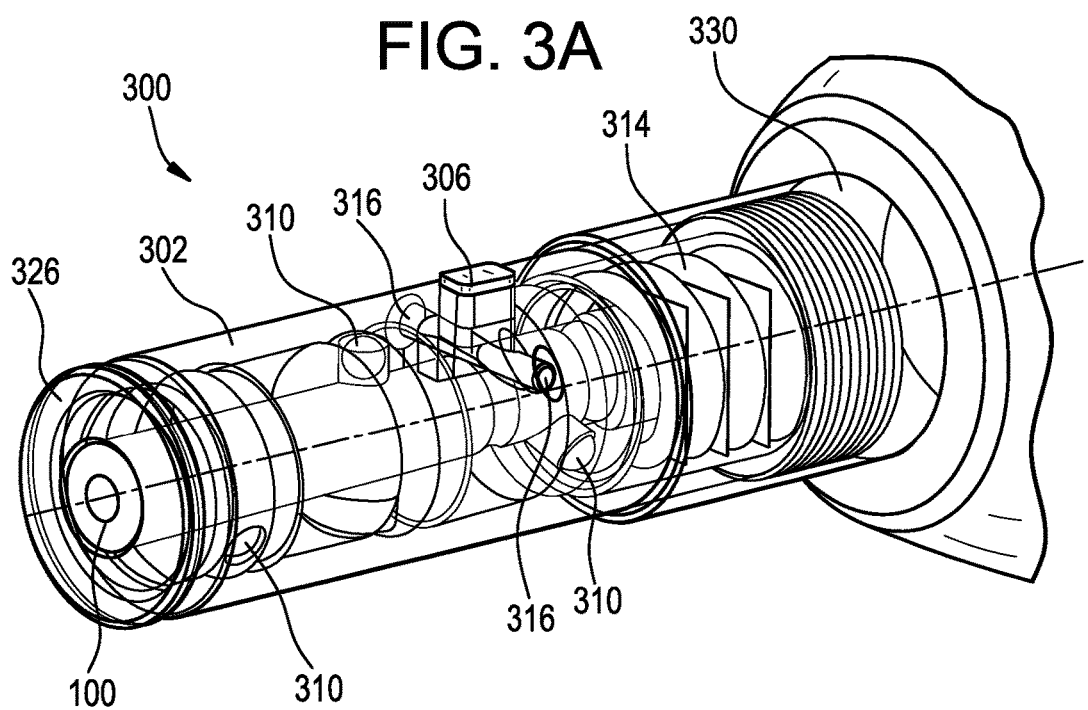
FIG. 3A is a perspective view of a coupling with an instrument inserted into the coupling, with a housing of the coupling shown as transparent.
Figure 3B:
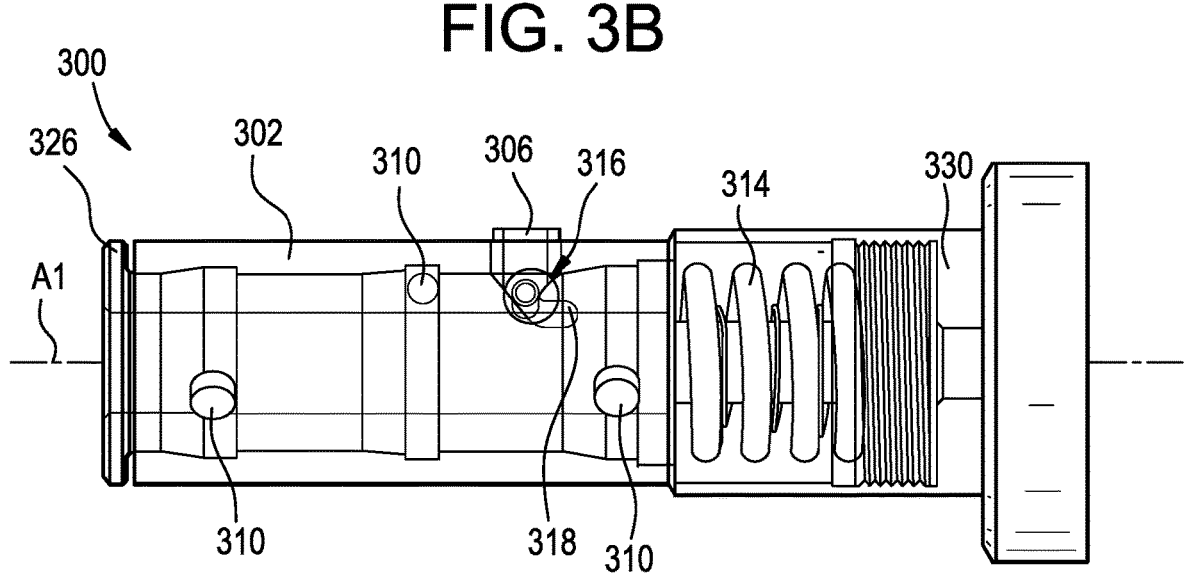
FIG. 3B is a side view of the coupling of FIG. 3A, with a housing of the coupling shown as transparent.
Figure 3C:
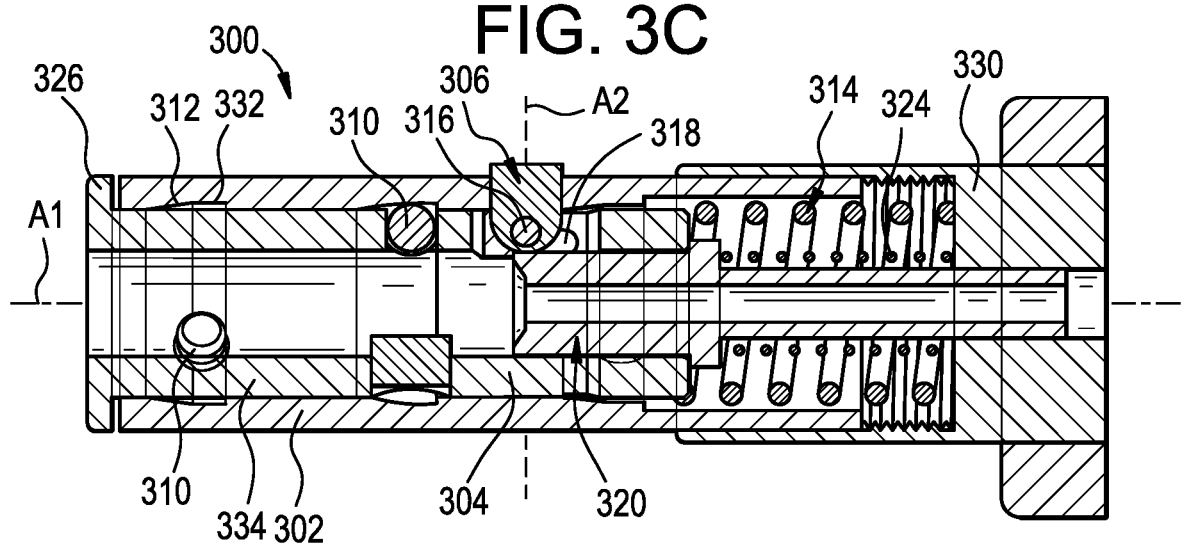
FIG. 3C is sectional side view of the coupling of FIG. 3A in an open position.
Figure 3D:
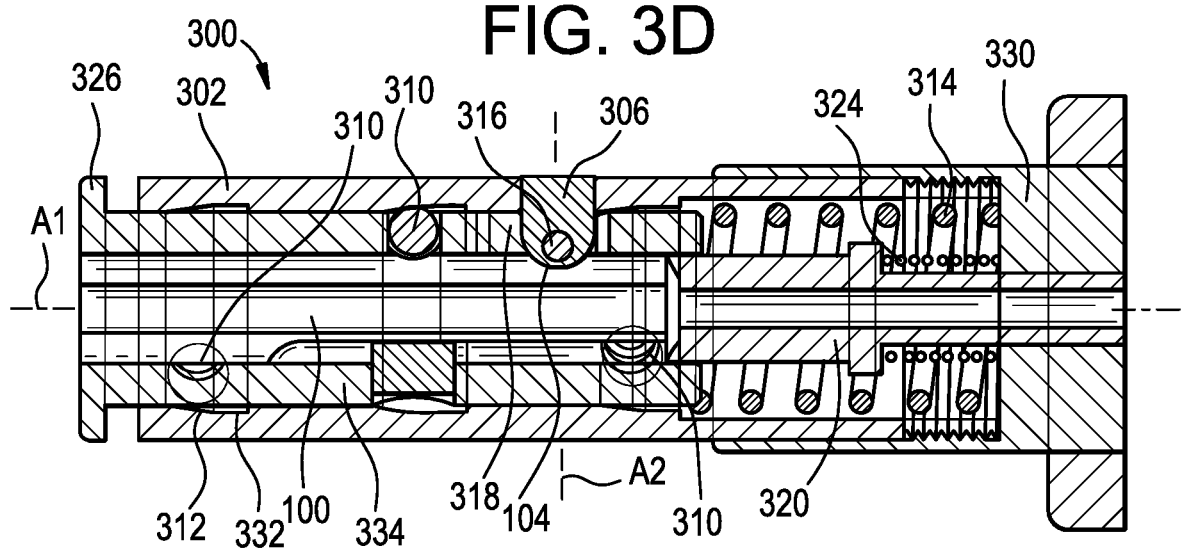
FIG. 3D is a sectional side view of the coupling of FIG. 3A in a closed position.

The coupling 300 can include clamping elements 310 in the form of a plurality of spherical balls, e.g., as shown in FIGS. 3A-3B. While various numbers of clamping elements 310 and various positioning of clamping elements can be used, the illustrated embodiment includes five balls distributed on three planes. A first pair of two clamping elements 310 can be arranged along a first axis parallel to the axis A1 (the lower clamping elements in FIG. 3A), a second pair of two clamping elements 310 can be arranged along a second axis parallel to the axis A1 (the lower clamping elements in FIG. 3D), and a fifth clamping element 310 can be arranged along a third axis parallel to the axis A1. The first, second, and third axes can be spaced equally from each other about the circumference of a circle that is concentric with the axis A1. The illustrated arrangement of clamping elements 310 can advantageously provide a clamping structure that is neither over-constrained nor under-constrained, helping to ensure a stable, toggle-free connection to the instrument 100.

Figure 3E:
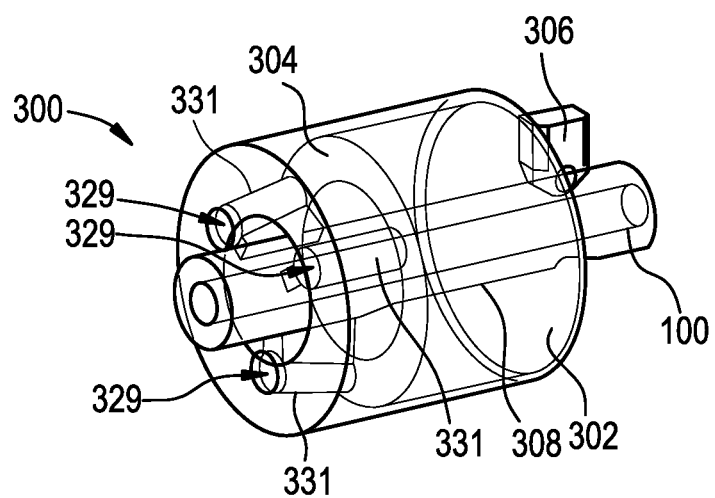
FIG. 3E is a perspective partial view of the coupling of FIG. 3A, shown with chuck-type clamping elements.

Alternatively, or in addition, the clamping elements 310 can include chuck-type jaws, e.g., as shown in FIG. 3E. The jaws 329 can be slidably mounted in ramped channels 331 formed in the coupling housing 302 and spaced about the circumference of the instrument channel 308. When the jaws 329 are urged distally by the clamp 304 as the coupling 300 is moved to the closed position, the jaws can ride along the ramped channels or tracks 331 and can be thereby urged radially-inward against an instrument 100 inserted through the coupling. Each jaw 329 can include a cylindrical portion received within a cylindrical portion of a respective channel 331 to retain the jaw in the channel while allowing the jaw to translate longitudinally along the channel. The cylindrical portion of the channel 331 can have a central longitudinal axis that extends at an oblique angle with respect to the axis A1 to direct the jaws 329 radially-inward when the clamp is actuated. The jaws 329 can include instrument-contacting surfaces with teeth or other surface treatments to better engage the instrument 100. The jaws 329 can have a broader contact surface area than some other clamping elements, which can advantageously make the coupling 300 less dependent on the stiffness, hardness, or other material properties of the instrument 100. For example, the risk of the jaws 329 digging into the instrument may be reduced by the increased surface area of the jaws.

Figure 4C:
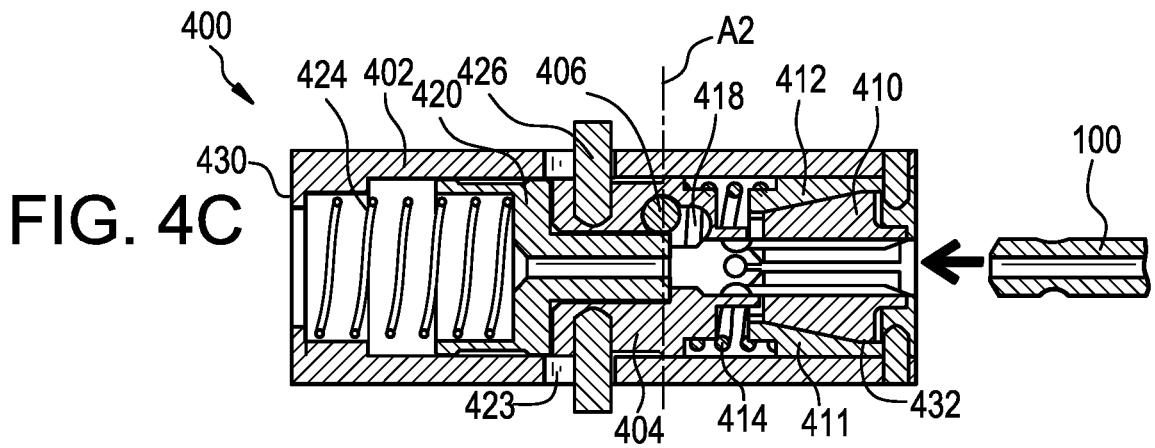
FIG. 4C is a sectional side view of the coupling of FIG. 4A in an open position.
Figure 4D:
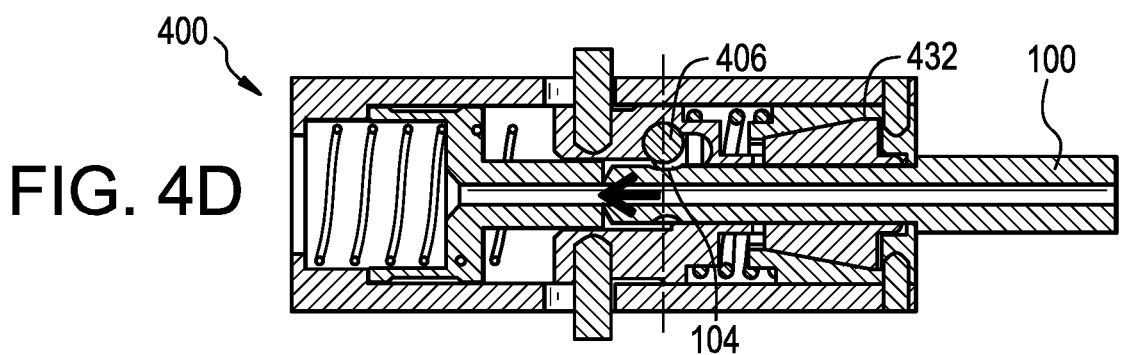
FIG. 4D is a sectional side view of the coupling of FIG. 4A transitioning from an open position to a closed position.
Figure 4E:
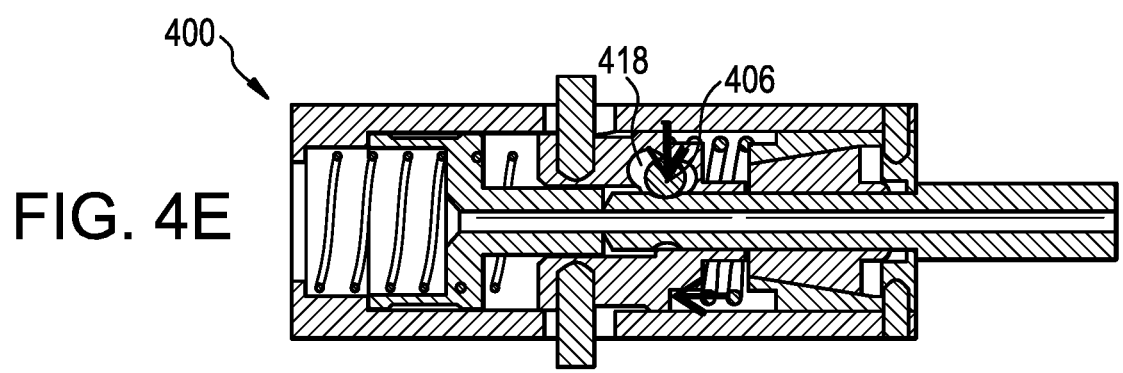
FIG. 4E is a sectional side view of the coupling of FIG. 4A transitioning from an open position to a closed position.
Figure 4F:
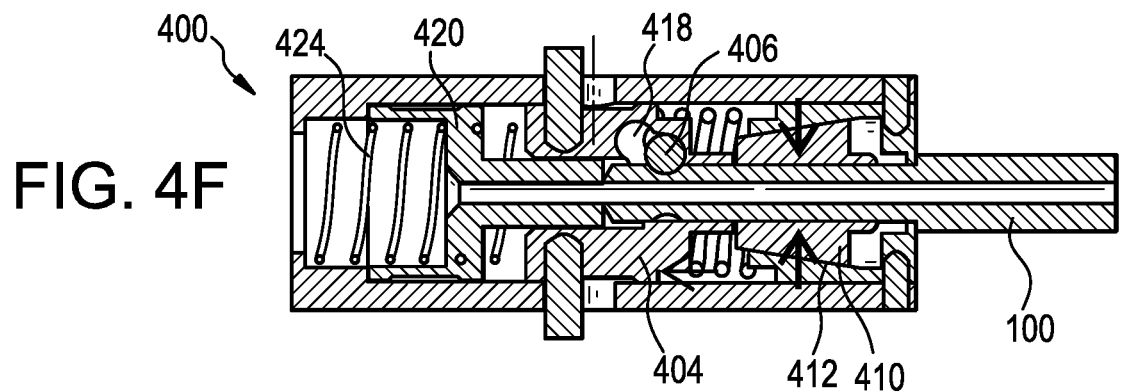
FIG. 4F is a sectional side view of the coupling of FIG. 4A in a closed position.
Figure 4G:
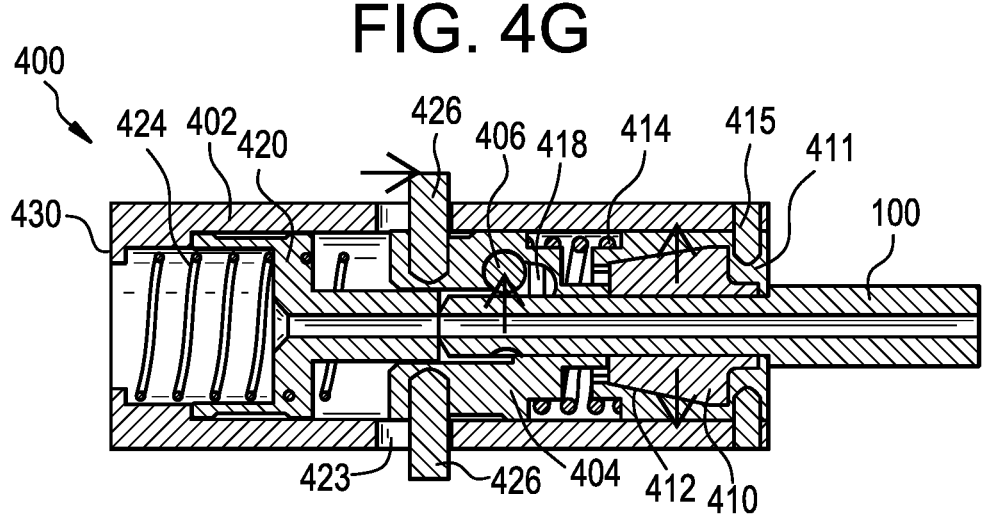
FIG. 4G is a sectional side view of the coupling of FIG. 4A transitioning from a closed position to an open position.
Figure 4H:
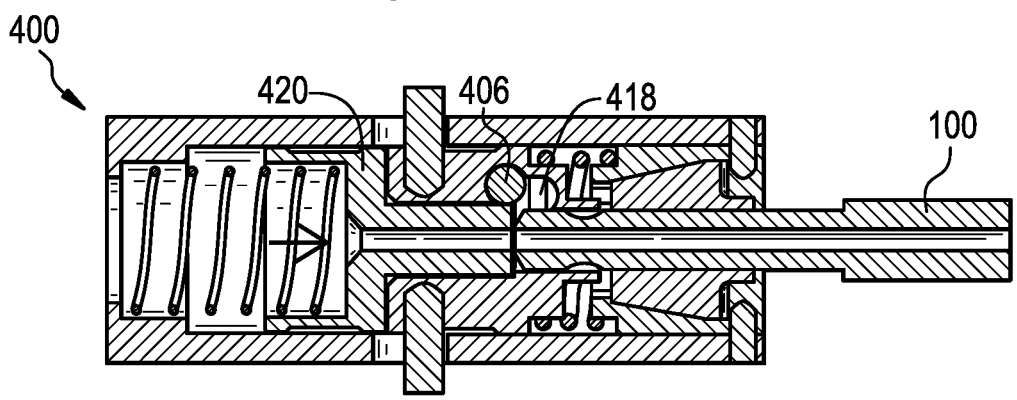
FIG. 4H is a sectional side view of the coupling of FIG. 4A transitioning from a closed position to an open position.
Figure 4I:
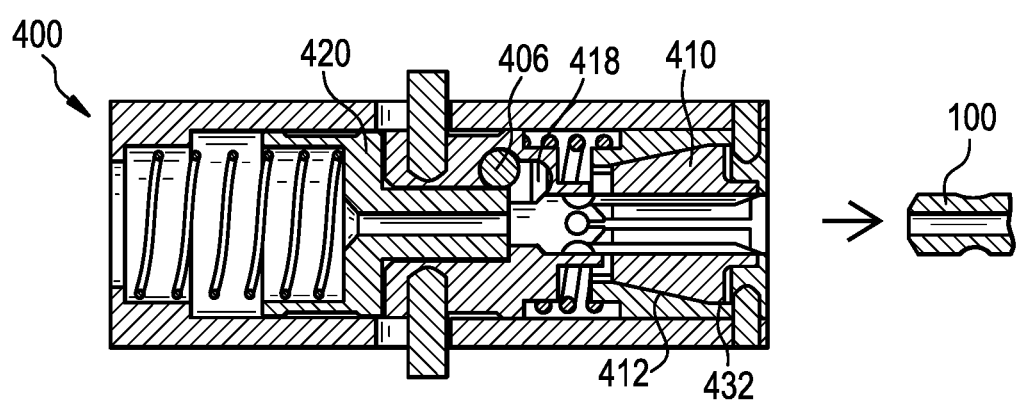
FIG. 4I is a sectional side view of the coupling of FIG. 4A in an open position.
Figure 4J:
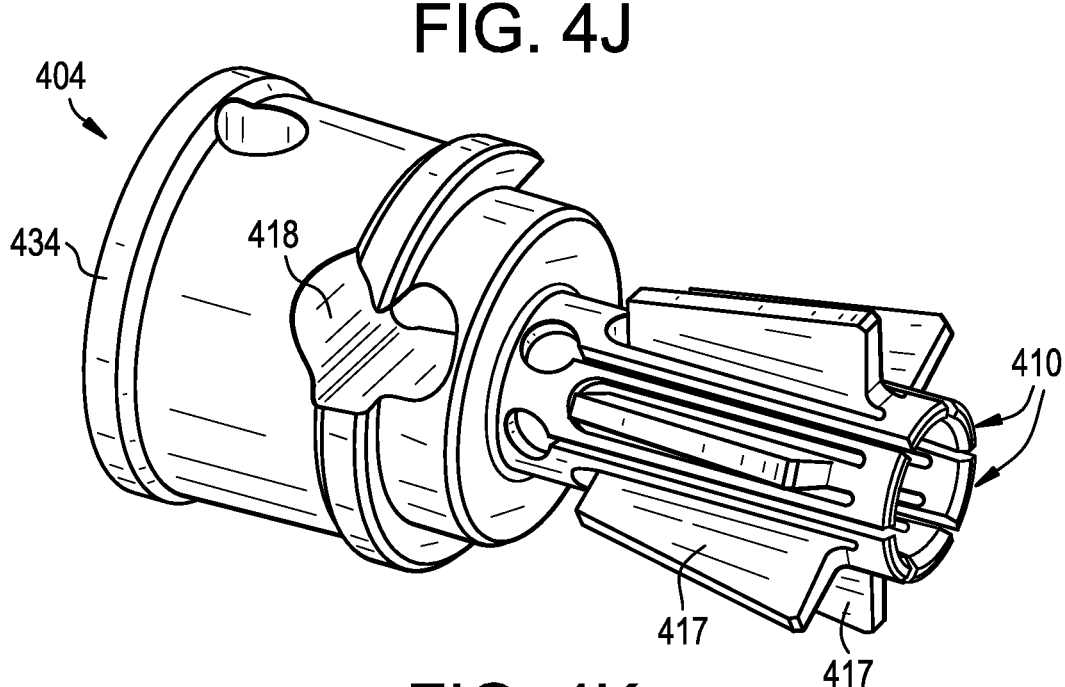
FIG. 4J is a perspective view of a clamp of the coupling of FIG. 4A.
Figure 4K:
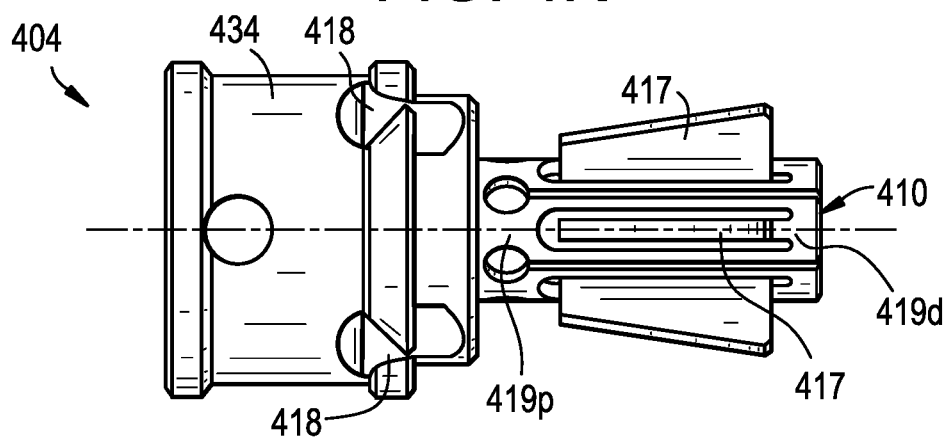
FIG. 4K is a top view of the clamp of FIG. 4J.
Figure 4L:
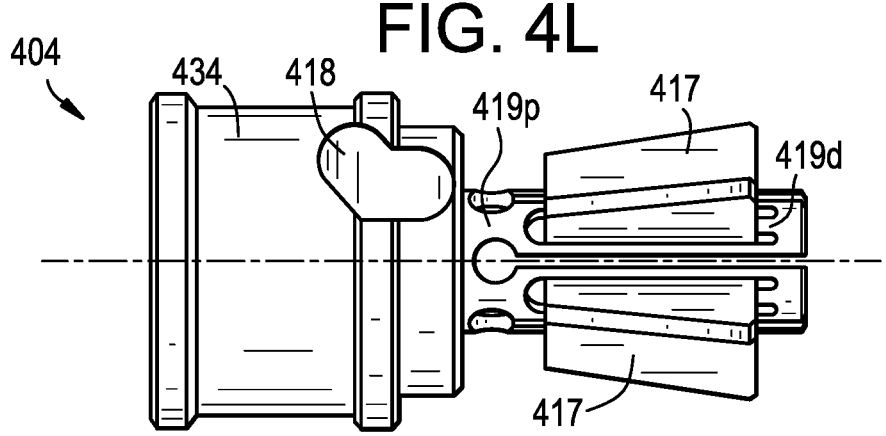
FIG. 4L is a side view of the clamp of FIG. 4J.
Figure 4Q:
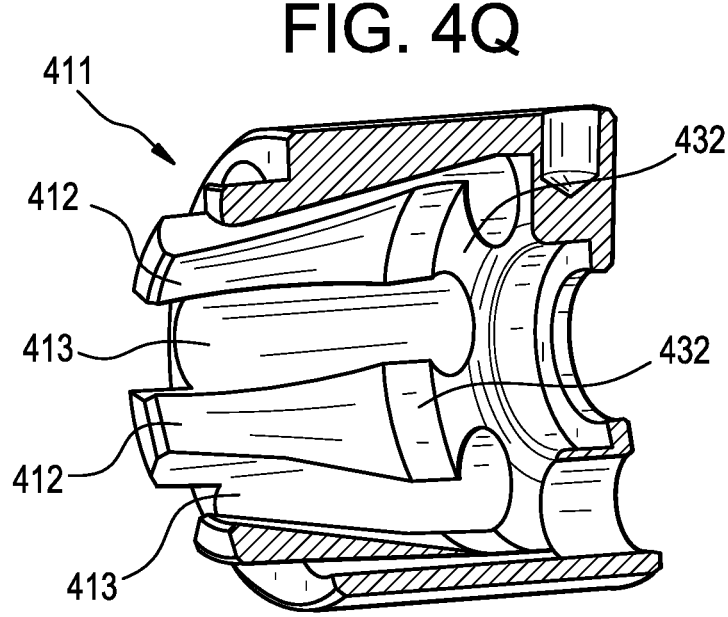
FIG. 4Q is a sectional perspective view of a nose of the coupling of FIG. 4A.
Figure 4R:
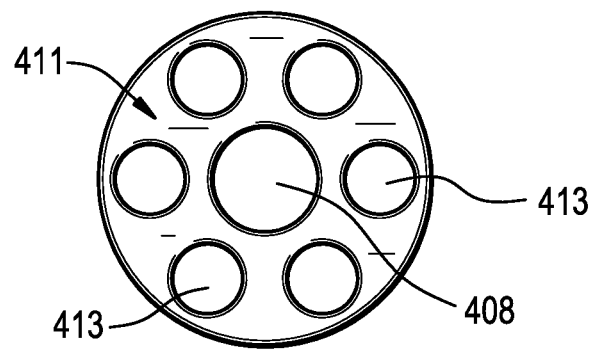
FIG. 4R is an end view of the nose of FIG. 4Q.

FIGS. 4A-4R illustrate an exemplary embodiment of an instrument coupling 400. The coupling 400 can be used to attach an instrument 100 to another instrument, object, or component. For example, the coupling 400 can be used to attach an instrument 100 to a navigation array 102.

The coupling 400 can include a housing 402 in which a clamp 404 and a slider 406 are disposed. The coupling 400 can define a channel 408 configured to receive at least a portion of an instrument 100 therein.

The clamp 404 can be configured to translate longitudinally within the housing 402 along a central axis of the housing A1. In a distal position, one or more clamping elements 410 of the clamp 404 can be free to move radially-outward, away from the central axis A1. In a proximal position, ramped inner surfaces 412 of the housing 402, or of a nose 411 inserted in the housing, can bear against the clamping elements 410 to urge the clamping elements radially-inward towards the axis A1, thereby clamping onto an instrument 100 disposed in the channel 408. The clamp 404 can be biased towards the proximal position by a clamp spring 414.

The slider 406 can be configured to translate laterally within the housing 402 along an axis A2 that is perpendicular to the central axis A1. In a first position, the slider 406 can interact with the clamp 404 via a slope slot 418 to hold the clamp in the distal, unclamped position. In a second position, the slider 406 can interact with the clamp 404 via the slope slot 418 to allow the clamp to move towards the proximal, clamped position under the bias of the clamp spring 414.

The coupling 400 can be movable between (i) an open position in which no instrument is received within the channel 408 and the coupling is prepared to receive an instrument, and (ii) a closed position in which an instrument is received within the channel and is securely engaged by the coupling to minimize or eliminate relative movement therebetween.

In the open position, as shown for example in FIG. 4C, an ejector 420 can be positioned within the clamp 404 to hold the slider 406 in the first position described above, thereby holding the clamp in the distal, unclamped position.

In the closed position, as shown for example in FIG. 4F, insertion of an instrument 100 into the channel 408 can displace the ejector 420 proximally against the bias of an ejector spring 424. When the ejector 420 is moved out of the path of the slider 406, the slider can be free to move to the second position described above, thereby releasing the clamp 404 to move to the proximal, clamped position.

To release the instrument 100 and return the coupling 400 to the open position, one or more release pins 426 can be pushed distally, e.g., by manual user input. Distal movement of the release pin 426 can compress the clamp spring 414 and move the clamp 404 to the distal, unclamped position. This movement of the clamp 404 can also move the slider 406 back to the first position, allowing the ejector 420 to move back into the path of the slider, pushing the instrument 100 out of the coupling 400 and once again holding the coupling in the open position.

The coupling 400 can thus allow for quick and toggle-free connection to an instrument. In some embodiments, the single step of pushing the instrument into the coupling can automatically lock the instrument to the coupling in a toggle-free manner, without requiring any additional steps or additional tools. Similarly, in some embodiments, the instrument can be released and the coupling reset in a single step, without requiring any additional steps or additional tools.

The housing 402 can include a generally tubular body having proximal and distal ends 402p, 402d and a central longitudinal axis A1. The body of the housing 402 can define a central lumen or cavity 408 that extends between the proximal and distal ends 402p, 402d. The proximal end 402p of the housing 402 can include a shoulder 430. The navigation array 102 can be integrally formed with the housing 402 or can be attached thereto via various attachment mechanisms, such as a threaded, welded, snap-fit, interference, or other connection. As discussed above with respect to FIGS. 2U-2X, the navigation array 102 can be coupled to a handle assembly 264 in which the housing 402 is rotatably mounted. The exterior surface of the housing 402 can include ribs, flanges, shoulders, or various other features for aligning, retaining, or otherwise interacting with such a handle assembly, as described above.

The interior surface of the housing 402 can include surface features 412 for urging the clamping elements 410 of the clamp 404 radially-inward when the clamp translates longitudinally within the housing. The surface features 412 can be formed in an integral sidewall of the housing 402, or in a nose insert 411 disposed within the housing as shown. In the illustrated embodiment, the interior surface of the nose 411 includes one or more conically-tapered sections 412. Each conical section 412 can be disposed adjacent to a cylindrical section 432. The cylindrical section 432 can have a diameter equal to or greater than the base diameter of the conical sections 412. Accordingly, when longitudinally-aligned with the cylindrical section 432, the clamping elements 410 can be free to move radially-outward, e.g., to disengage from an instrument 100. When longitudinally-aligned with the conical sections 412, the clamping elements 410 can be urged radially-inward, e.g., to engage an instrument 100. While six conical sections 412 are shown, it will be appreciated that the nose 411 can include any number of surface features, and that the surface features can instead be curved, stepped, or otherwise arranged to urge the clamping elements 410 inward. The illustrated surface features 412 are formed only in discrete positions about the circumference of the nose 411, which positions are aligned with the clamping elements 410, though in other arrangements the surface features can extend around the entire inner circumference of the nose 411.

As shown in FIGS. 4Q-4R, the nose 411 can include one or more reliefs 413 that are offset from the conical sections 412 about the inner circumference of the nose. The reliefs 413 can receive the clamping elements 410 during initial assembly of the coupling 400 to allow the nose 411 to be passed longitudinally over the clamping elements and into the housing 402. Once the ramped portions 412 of the nose 411 are inserted into the housing 402 beyond the ramped surfaces of the clamping elements 410, the nose can be rotated relative to the housing about the axis A1 to rotationally align the ramped portions of the nose with the ramped portions of the clamping elements. The nose 411 can thus be assembled to the coupling 400 without compressing the clamping elements 410. The reliefs 413 can be formed by respective cylindrical holes extending axially through the nose 411. The reliefs 413 can also facilitate cleaning and/or sterilization of the coupling 400. The nose 411 can be retained within the housing 402 by one or more assembly pins 415 or other retention features. The nose 411 can include a central opening into the coupling channel 408 through which an instrument can be received. The central opening can have a diameter that is equal to or only slightly greater than an outside diameter of the instrument. Accordingly, the nose 411 can protect the clamping elements 410 from being damaged during insertion of the instrument.

As shown in FIGS. 4J-4L, the clamp 404 can include a cage 434 from which one or more clamping elements 410 extend. The clamping elements 410 can be configured to move radially-inward or radially-outward in response to longitudinal movement of the clamp 404 within the housing 402. For example, the clamp 404 can include a plurality of fingers 410 that extend distally from the cage 434. The fingers 410 can collectively define an inner channel in which an instrument 100 can be received. The fingers 410 can be flexible and/or resilient. Each finger 410 can include an inner instrument-contacting surface. The instrument-contacting surface can form a negative of an instrument with which the coupling 400 is to be used. For example, the instrument-contacting surface can be concave and/or can define a section of a cylinder, and can have a radius that is equal or substantially equal to a radius of the instrument 100. Each finger 410 can include a fin 417 that projects radially-outward therefrom to engage a corresponding ramped surface 412 of the nose 411. The fin 417 can have a nose-contacting surface that is ramped, curved, or otherwise tapered such that a radial dimension of the fin is greater at the distal end of the fin than at the proximal end. For example, the nose-contacting surface of the fin 417 can extend at an oblique angle with respect to the axis A1.

Each finger 410 can include one or more joints or flex points to allow the fin 417 to move radially-inward and radially-outward relative to the cage 434. The illustrated fingers 410 each include a proximal flex point 419p and a distal flex point 419d. The proximal and distal flex points 419p, 419d can be formed by a double cut of the clamp material, e.g., a first cut that defines a cantilevered finger 410 extending distally from the cage 434 and a second cut that defines a cantilevered fin 417 extending proximally from a distal end of the finger. The proximal flex point 419p can be formed by a region of reduced material thickness, e.g., formed by circular cut-outs where the cantilevered finger 410 meets the cage 434. The proximal flex point 419p can allow the finger 410 to bend radially relative to the cage 434. The distal flex point 419d can be formed by a region of reduced material thickness, e.g., formed where the cantilevered fin 417 meets the distal end of the finger 410. The distal flex point 419d can allow the fin 417 to bend radially relative to the finger 410.

As shown in FIG. 4M, during actuation of the clamp 404, the fingers 410 can bend at both the proximal and distal flex points 419p, 419d to allow parallel or substantially parallel displacement of the fins 417. In other words, the instrument-contacting surface of the fins 417 can remain at a constant or substantially constant angle with respect to the axis A1 as the clamp 404 moves between the open and closed positions. In some embodiments, the angle can be zero such that the instrument-contacting surfaces of the fins 417 remain parallel to the axis A1 as the clamp 404 moves between the open and closed positions. This parallel displacement can advantageously maximize the contact surface area between the fingers 410 and the instrument 100, reducing wear and providing increased resistance to relative movement between the instrument and the coupling 400.

While the illustrated clamp 404 includes six clamping elements 410 spaced equally about the circumference of the clamp, in other arrangements, the clamp 404 can include a greater or lesser number of clamping elements and/or clamping elements spaced in other positions.

As shown in FIGS. 4N-4O, the inner channel of the clamp 404 can include a non-cylindrical portion 421. The non-cylindrical portion 421 can be formed by a flat section of the channel that protrudes radially-inward into the channel. The non-cylindrical portion 421 can engage with a corresponding flat or other non-cylindrical portion of the instrument 100 to limit or prevent rotation of the instrument relative to the clamp 404 about the axis A1. The non-cylindrical portion 421 can also prevent use of the coupling 400 with unauthorized or unintended instruments, e.g., instruments lacking a corresponding flat or other feature.

As shown in FIG. 4P, the fins 417 can have a large radial dimension H, which can advantageously allow the instrument contact surface length C and the cone angle α to be increased. Increasing the contact surface length C can increase the overall stability of the clamp 404. Increasing the cone angle α can help prevent the clamp 404 from self-locking. In other words, the cone angle α can be made sufficiently large to allow the clamp 404 to be released easily for a given clamp spring force. In some embodiments, the cone angle α can be at least about 10 degrees.

The clamp 404 can be mechanically-linked to the slider 406, e.g., such that movement of the slider results in movement of the clamp and vice versa. The clamp 404 can include a slot 418 in which the slider 406 is movably disposed. At least a portion of the slot 418 can be sloped such that, when the slider 406 is received in the sloped portion of the slot, translation of the slider 406 along the axis A2 causes translation of the clamp 404 along the axis A1 and vice versa. The sloped portion of the slot 418 can extend at an oblique angle with respect to the axis A1 and at an oblique angle with respect to the axis A2. The slot 418 can include a non-sloped portion. The non-sloped portion of the slot 418 can extend parallel to the axis A1 and perpendicular to the axis A2. When the slider 406 is disposed in the non-sloped portion of the slot 418, the clamp 404 can move longitudinally along the axis A1 (at least to the extent permitted by the length of the slot) without moving the slider 406 along the axis A2. The slot 418 can include a single sloped portion or a plurality of sloped portions. The slot 418 can include a single non-sloped portion or a plurality of non-sloped portions.

Referring again to FIGS. 4B-4I, one or more release pins 426 can be coupled to the clamp 404 and can extend through respective slots 423 formed in the housing 402. For example, the release pins 426 can be press-fit, welded, or otherwise attached to holes formed in the clamp 404. While cylindrical pins 426 are shown, it will be appreciated that the release pins can have any of a variety of shapes that facilitate application of a longitudinal force thereto by a user. In use, as described further below, the release pins 426 can be urged distally relative to the housing 402 to push the clamp 404 distally and release the clamping elements 410 from an instrument 100 received within the coupling 400 to detach the instrument from the coupling.

The slider 406 can be mounted within a transverse throughbore 450 of the housing 402 sized to receive the slider 406 therethrough. The transverse throughbore 450 can have a height along the axis A2 that is greater than a height of the slider 406 along the axis A2, such that the slider can translate within the transverse throughbore along the axis A2. The slider 406 can engage the slot 418 of the clamp to prevent rotation of the clamp 404 relative to the housing 402 about the axis A1. The transverse throughbore 450 can secure the slider 406 at a fixed or substantially fixed longitudinal position within the housing 402.

The slider 406 can be formed by a pin or beam inserted through the transverse throughbore 450 and the slot 418. The slider 406 can act as an engagement feature for engaging with an instrument 100 in certain positions of the slider to help secure the instrument within the coupling 400. For example, at least a portion of the slider 406 can be received within a corresponding depression or recess 104 of an instrument 100. Engagement between the slider 406 and the depression 104 can be effective to lock an axial position of the instrument 100 with respect to the coupling 400. The proximal-facing surface of the slider 406 and/or the distal-facing surface of the slider can be curved, ramped, or otherwise tapered. For example, the slider 406 can be formed as a cylinder extending perpendicular to the axes A1 and A2 as shown. Such features can interact with corresponding surface geometry of the instrument depression 104 to center the slider 406 within the recess and/or to push or pull the instrument 100 to a predetermined longitudinal position relative to the coupling 400.

The slot 418 of the clamp 404 can intersect with a central channel of the clamp in which the ejector 420 and/or the instrument 100 can be received. When the ejector 420 is positioned at this intersection, translation of the slider 406 along the axis A2 can be prevented by interference between the ejector and the slider. When an instrument 100 is inserted into the coupling 400 to move the ejector 420 out of this intersection, the ejector no longer interferes with translation of the slider 406 along the axis A2, and the slider can be free to move into engagement with the instrument depression 104.

The shoulder 430 can define a distal-facing spring seat. For example, the ejector spring 424 can be disposed between a distal-facing surface of the shoulder 430 and a proximal-facing surface of the ejector 420, such that the ejector is biased distally away from the shoulder. The clamp spring 414 can be disposed between a proximal-facing surface of the nose 411 and a distal-facing surface of the clamp 404, such that the clamp is biased proximally away from the nose 411. While coil springs are shown for the ejector spring 424 and the clamp spring 414, alternative bias elements can be used for one or both springs, such as wave springs, leaf springs, and the like.

While not shown, the coupling 400 can include a mating geometry, e.g., of the type described above with respect to the mating geometry 262. The mating geometry can extend proximally from the housing 402. The mating geometry can be the same as the mating geometry of an instrument 100 with which the coupling 400 is to be used, or can differ in one or more respects. The mating geometry can include one or more flats, e.g., to facilitate torque application to the coupling 400 and an instrument 100 received therein about the axis A1. The mating geometry can allow the coupling 400 to be connected to various other instruments or components, such as a drill, a driver, a knob or handle, a navigation array, and so forth. The mating geometry, the housing 402, and/or the ejector 420 can be cannulated. The cannulation can be configured to align with a corresponding cannulation of an instrument 100 when the instrument is received within the coupling 400. The cannulation can allow the coupling 400 and an instrument 100 received therein to be inserted over a guidewire, or can allow cement or other flowable material to be delivered through the coupling and an instrument received therein.

The ejector 420 can be defined by a generally cylindrical plunger body. A proximal portion of the ejector 420 can be slidably mounted in the housing 402, and can be biased distally by the ejector spring 424. A distal portion of the ejector 420 can be slidably mounted in the channel of the clamp 404.

The coupling 400 can be configured such that the central channel of the housing 402, the ejector 420, the clamp 404, and the nose 411 all have the same or substantially the same diameter. By forming one or more of these components with a single relevant diameter, concentric tolerances can be reduced or eliminated, improving the overall precision of the coupling.

An exemplary instrument mating geometry is shown in FIG. 4A. It will be appreciated that the illustrated geometry is exemplary and that the coupling 400 can be used with any of a variety of instruments having any of a variety of mating geometries. In some embodiments, the mating geometry of the instrument can be a cylindrical shaft. In some embodiments, the mating geometry of the instrument can be a cylindrical shaft with one or more flats formed therein.

As shown in FIG. 4A, the instrument 100 can include a generally cylindrical shaft 106 with a mating geometry at or near the proximal end of the shaft. The distal end of the shaft (not shown) can include the functional operating features of the instrument 100, such as an end effector, blade, rasp, tap, drill, etc. The instrument shaft 106 can be cannulated, e.g., to allow the instrument 100 to be inserted over a guidewire or to allow cement or other flowable materials to be delivered through the instrument.

The mating geometry can include a section of the instrument shaft 106 with one or more flats 108. For example, the mating geometry can include a section of the instrument shaft 106 having a rectangular or substantially rectangular transverse cross-section. The flats 108 of the mating geometry can interact with the non-cylindrical section 421 of the clamp 404 to limit or prevent rotation of the instrument shaft 106 relative to the coupling 400 about the axis A1. This can allow, in some instances, for torque about the axis A1 applied to the coupling 400 to be transferred to the instrument 100 and vice versa.

The mating geometry can include at least one depression or recess 104 configured to engage with the slider 406, as described above. The depression 104 can interact with the slider 406 to limit or prevent axial translation of the instrument 100 relative to the coupling 400 along the axis A1. The depression 104 can be formed in the same portion of the instrument shaft in which the one or more flats 108 are formed.

The mating geometry can include a bulleted or tapered proximal-most tip 110. The mating geometry can include ramped, curved, or otherwise tapered transitions 112 from the one or more flats 108 to the cylindrical outside diameter of the instrument shaft. Such features can act as lead-in surfaces, urging the clamping elements 410 of the coupling 400 radially-outward as the instrument 100 is initially inserted into the coupling. One or more of the transitions 112 can be longitudinally-offset from each other along the length of the instrument 100. As noted above, the outside radius of the portion of the instrument shaft received within the clamp 404 can be equal or substantially equal to the radius of the bearing surfaces of the clamping elements 410.

The mating geometry can be keyed such that the instrument 100 can only be inserted into the coupling 400, and in particular into the clamp 404, in one orientation or in a limited number of orientations. This can help ensure that the depression 104 of the instrument 100 is aligned with the slider 406. This can also help ensure that the navigation array 102 is coupled to the instrument 100 in a predetermined or known orientation, which may be necessary when navigating an asymmetrical instrument.

In use, the coupling 400 can be used to attach an instrument 100 to another instrument, object, or component. For example, the coupling 400 can be used to attach an instrument 100 to a navigation array 102.

The coupling 400 can be movable between (i) an open position in which no instrument is received within the channel 408 and the coupling is prepared to receive an instrument, and (ii) a closed position in which an instrument is received within the channel and is securely engaged by the coupling to minimize or eliminate relative movement therebetween.

FIG. 4C illustrates the coupling 400 in the open position. As shown, the ejector 420 can be positioned within the clamp 404 at the intersection with the slot 418, preventing translation of the slider 406 along the axis A2 and holding the slider in a first position. The ejector 420 can be maintained at this position by the bias of the ejector spring 424 urging the ejector distally away from the shoulder 430. With the slider 406 in the first position, the slider 406 can be positioned at the upper end of the sloped portion of the clamp slot 418. Because the slider 406 is prevented by the ejector 420 from translating along the axis A2, the slider 406 cannot travel within the clamp slot 418 and therefore the slider holds the clamp 404 in a distal, unclamped position. In particular, in the distal, unclamped position of the clamp 404, the clamping elements 410 can be longitudinally aligned with the relief portions 432 of the inner surface of the nose 411, such that the clamping elements are free to move radially-outward away from the axis A1. In the distal, unclamped position, the clamp spring 414 can be compressed between the clamp 404 and the nose 411.

FIGS. 4D-4F illustrate the coupling 400 transitioning from the open position to the closed position. As shown, insertion of an instrument 100 into the channel 408 can displace the ejector 420 proximally, compressing the ejector spring 424 and moving the ejector out of the intersection with the slot 418. When the ejector 420 is moved out of the path of the slider, the slider 406 can be free to translate along the axis A2 and out of the first position. With the slider 406 no longer being held in the first position, the slider can travel within the clamp slot 418 and therefore the clamp 404 is released to translate longitudinally within the housing 402. The bias force supplied by the clamp spring 414 can urge the clamp 404 proximally, thereby guiding the clamping elements 410 along the ramped bearing surfaces 412 of the nose 411 to move the clamping elements radially inward into firm engagement with the instrument 100. As the clamp 404 moves proximally under the force of the clamp spring 414, the slider 406 can travel along the sloped portion of the clamp slot 418, urging the slider 406 into a second position in which the slider is seated in the depression 104 of the instrument 100.

Once the slider 406 is in the second position, the slider can travel along the non-sloped portion of the clamp slot 418 to allow the clamp 404 to continue advancing proximally to the extent needed to clamp the instrument 100, thereby positioning the coupling 400 in the closed position.

In the closed position, the slider 406 can be received within the depression 104 of the instrument 100 to limit or prevent translation of the instrument along the axis A1 relative to the coupling 400, e.g., limiting or preventing surging movement, and/or to limit or prevent rotation of the instrument 100 about the axis A1 relative to the coupling 400, e.g., limiting or preventing roll movement. Also in the closed position, the clamping elements 410 can be wedged against the exterior surface of the instrument 100 to limit or prevent lateral translation of the instrument relative to the coupling 400, to limit or prevent translation of the instrument along the axis A1 relative to the coupling 400, to limit or prevent rotation of the instrument 100 about the axis A1 relative to the coupling 400, and/or to limit or prevent pivoting movement of the instrument relative to the coupling 400, e.g., limiting or preventing heaving, swaying, surging, rolling, pitching, and/or yawing movement. The coupling 400 can thus limit or prevent movement of the instrument 100 relative to the coupling in at least six degrees of freedom. It will be appreciated that, in some embodiments, the coupling 400 can be configured to preserve one or more of these degrees of freedom.

FIGS. 4G-4I illustrate the coupling 400 transitioning from the closed position to the open position to release the instrument 100 therefrom. To release the instrument 100 and return the coupling 400 to the open position, one or more of the release pins 426 can be pushed distally, e.g., by manual user input. Distal movement of the release pins 426 can move the clamp 404 distally relative to the housing 402 to the distal, unclamped position, compressing the clamp spring 414. With the clamping elements 410 now offset from the ramped bearing surfaces 412 of the nose 411, the clamping elements can be free to move radially-outward to disengage from the instrument 100. As the clamp 404 moves distally, the slider 406 can travel along the clamp slot 418, forcing the slider to translate along the axis A2 to the first position. This movement of the slider 406 can remove the slider from the depression 104 of the instrument 100, allowing the instrument to move axially relative to the coupling 400. Accordingly, the ejector 420 can be again free to slide distally into the path of the slider 406, under the bias force of the ejector spring 424. Distal movement of the ejector 420 can urge the instrument 100 distally out of the channel 408 of the coupling 400. When the user-applied force is removed from the release pins 426, the ejector 420 can remain in the path of the slider 406, holding the coupling 400 in the open position described above such that the coupling is ready to be coupled to an instrument 100.

To assemble the coupling 400, the ejector spring 424, the ejector 420, the clamp 404, and the clamp spring 414 can be loaded in order into the proximal end of the housing 402. The release pins 426 and the slider 406 can then be inserted through openings 423, 450 in the housing 402 into the clamp 404. The nose 411 can be inserted into the housing 402 with the reliefs 413 being rotationally aligned with the fins 417 of the clamp 404. Once the nose 411 is fully inserted into the housing 402, the nose can be rotated about the axis A1 to rotationally align the ramping surfaces 412 of the nose with the fins 417 of the clamp 404. The assembly pins 415 can then be inserted through openings in the housing 402 and into the nose 411 to retain the nose in position and complete the assembly.

Figure 4S:
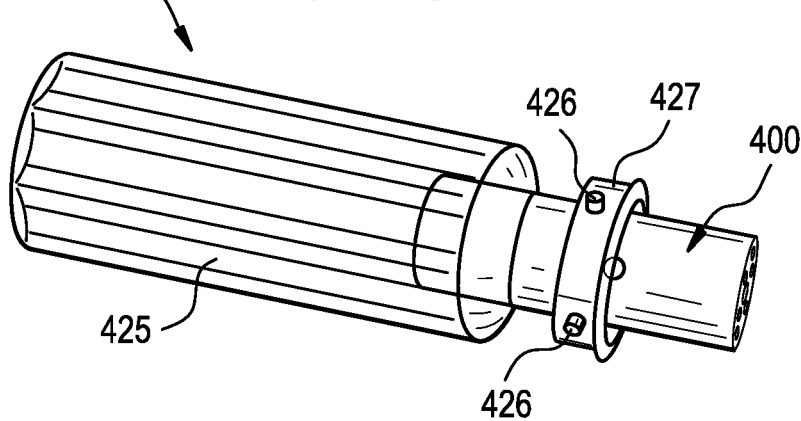
FIG. 4S is a perspective view of the coupling of FIG. 4A and a handle assembly, with the handle assembly shown as transparent.

The coupling 400 can be used to attach an instrument 100 to another instrument, object, or component. For example, the coupling 400 can be used to attach an instrument 100 to a navigation array 102. The navigation array or other component can be attached directly to the outer housing 402 of the coupling 400, or can be coupled thereto via one or more intermediate components. For example, the coupling 400 can be used with the handle assembly 264 described above. As another example, as shown in FIG. 4S, the coupling 400 can be used with a handle assembly 464. The handle assembly 464 can include a gripping portion 425, e.g., for applying torque to the coupling 400 and an instrument inserted therein about the axis A1. The handle assembly 464 can also include an actuator 427, e.g., to facilitate actuation of the release pins 426 to eject an instrument from the coupling 400. A navigation array or other component can be attached to the handle assembly 464.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The devices disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth. The various components of the devices disclosed herein can be rigid or flexible. One or more components or portions of the device can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices and methods disclosed herein can be used in minimally-invasive surgery and/or open surgery. While the devices and methods disclosed herein are generally described in the context of spinal surgery on a human patient, it will be appreciated that the methods and devices disclosed herein can be used in any type of surgery on a human or animal subject, in non-surgical applications, on non-living objects, and so forth.

Although specific embodiments are described above, it should be understood that numerous changes may be made within the spirit and scope of the concepts described.

The invention claimed is:

1. A coupling device, comprising:
  a housing having proximal and distal ends and a central longitudinal axis A1 extending therebetween;
  a clamp having a plurality of clamping elements and defining an instrument channel, the clamp being longitudinally-slidable within the housing between an unclamped position in which the clamping elements are free to move radially outward away from the axis A1 and a clamped position in which the clamping elements are urged radially-inward towards the axis A1; and
  a slider laterally translatable relative to the housing between a first position in which an engagement feature of the slider is disposed in the instrument channel and a second position in which the engagement feature is radially offset from the instrument channel;
  wherein the slider in the second position maintains the clamp in the unclamped position and wherein the slider in the first position allows the clamp to move to the clamped position.

2. The device of claim 1, wherein the slider is movable between the first and second positions by translating the slider relative to the housing along an axis A2 that is perpendicular to the axis A1.

3. The device of claim 1, wherein the slider comprises a pin received within a slot formed in the clamp.

4. The device of claim 3, wherein the slot includes a sloped portion that extends at an oblique angle relative to the axis A1 and a non-sloped portion that extends parallel to the axis A1.

5. The device of claim 1, wherein the engagement feature of the slider comprises a protrusion formed in an opening of the slider, the opening being configured to receive an instrument therethrough when the instrument is inserted into the coupling.

6. The device of claim 1, wherein the engagement feature of the slider comprises an exterior surface of the slider.

7. The device of claim 1, wherein the slider is mounted in a slider cage, the slider cage being longitudinally-translatable within a cavity of the clamp and being longitudinally-fixed relative to the housing.

8. The device of claim 1, wherein the slider is mounted in a transverse throughbore of the housing.

9. The device of claim 1, wherein the clamp is biased towards the clamped position by a clamp spring.

10. The device of claim 1, further comprising a release element to which a force can be applied along the axis A1 to move the clamp to the unclamped position.

11. The device of claim 1, further comprising an instrument configured to be selectively attached to the coupling, the instrument including a recess that is engaged by the slider when the instrument is received within the instrument channel to axially retain the instrument within the coupling.

12. A coupling device, comprising:
a housing having proximal and distal ends and a central longitudinal axis A1 extending therebetween;
a clamp having a plurality of clamping elements and defining an instrument channel, the clamp being longitudinally-slidable within the housing between an unclamped position in which the clamping elements are free to move radially outward away from the axis A1 and a clamped position in which the clamping elements are urged radially-inward towards the axis A1;
a slider movable relative to the housing between a first position in which the clamp is allowed to move to the clamped position and a second position in which the clamp is maintained in the unclamped position; and
an ejector that holds the slider in the first position when no instrument is inserted in the instrument channel and is configured to eject an instrument from the instrument channel, wherein insertion of an instrument into the instrument channel displaces the ejector to allow the slider to move to the second position.

13. The device of claim 1, further comprising an ejector that holds the slider in the second position when no instrument is inserted in the instrument channel.

14. The device of claim 13, wherein insertion of an instrument into the instrument channel displaces the ejector to allow the slider to move to the first position.

15. The device of claim 13, wherein the ejector is biased towards the slider by an ejector spring.

16. The device of claim 13, wherein the slider includes an opening having:
a first portion with a width W1 large enough to allow the ejector to enter the opening when the first portion is aligned with the instrument channel; and
a second portion with a width W2 that is less than the width W1, the second portion including a protrusion that defines the engagement feature of the slider and that is configured to engage an instrument disposed in the instrument channel when the second portion is aligned with the instrument channel.

17. The device of claim 1, wherein the clamping elements are urged radially-inward by an interior surface feature of the housing.

18. The device of claim 17, wherein the surface feature comprises a conical interior surface of the housing.

19. A coupling device, comprising:
a housing having proximal and distal ends and a central longitudinal axis A1 extending therebetween; and
a clamp having a plurality of clamping elements and defining an instrument channel, the clamp being longitudinally-slidable within the housing between an unclamped position in which the clamping elements are free to move radially outward away from the axis A1 and a clamped position in which the clamping elements are urged radially-inward towards the axis, wherein the plurality of clamping elements include at least one of:
(i) a roller having an axle supported by a cage portion of the clamp; and
(ii) a chuck jaw slidably mounted in a track formed in the housing, the track having a central longitudinal axis that extends at an oblique angle relative to the axis A1.

20. A coupling device, comprising:
a housing having proximal and distal ends and a central longitudinal axis A1 extending therebetween; and
a clamp having a plurality of clamping elements and defining an instrument channel, the clamp being longitudinally-slidable within the housing between an unclamped position in which the clamping elements are free to move radially outward away from the axis A1 and a clamped position in which the clamping elements are urged radially-inward towards the axis A1
wherein the clamp includes a first cage portion in which a first plurality of the clamping elements are disposed and a second cage portion in which a second plurality of the clamping elements are disposed.

21. The device of claim 20, wherein the first and second cage portions are longitudinally-translatable relative to one another.

22. The device of claim 20, wherein the first and second cage portions are biased apart from one another along the axis A1.

23. The device of claim 20, wherein the housing includes a proximal ramped portion that urges the clamping elements of the first cage portion radially-inward and a distal ramped portion that urges the clamping elements of the second cage portion radially-inward.

24. A coupling device, comprising:
a housing having proximal and distal ends and a central longitudinal axis A1 extending therebetween;
a clamp having a plurality of clamping elements and defining an instrument channel, the clamp being longitudinally-slidable within the housing between an unclamped position in which the clamping elements are free to move radially outward away from the axis A1 and a clamped position in which the clamping elements are urged radially-inward towards the axis A1; and
a handle assembly in which the coupling is rotatably mounted, wherein the handle assembly includes a bias element that biases the coupling distally along the axis A1 relative to the handle assembly.

25. A coupling device, comprising:
a housing having proximal and distal ends and a central longitudinal axis A1 extending therebetween;
a clamp having a plurality of clamping elements and defining an instrument channel, the clamp being longitudinally-slidable within the housing between an unclamped position in which the clamping elements are free to move radially outward away from the axis A1 and a clamped position in which the clamping elements are urged radially-inward towards the axis A1; and a handle assembly in which the coupling is rotatably mounted, wherein the handle assembly includes a locking element engaged with one or more teeth of the coupling to selectively maintain the coupling in a fixed rotational position about the axis A1 relative to the handle assembly.

26. A coupling device, comprising:

a housing having an instrument channel and a clamp; and a slider movable relative to the housing between a first position in which the clamp is allowed to move to a clamped position and a second position in which the clamp is maintained in an unclamped position, wherein insertion of an instrument into the instrument channel causes the clamp to translate longitudinally with respect to the instrument channel within the housing from the unclamped position to the clamped position to lock radial movement of the instrument relative to the housing, and wherein insertion of an instrument into the instrument channel also causes the slider to translate laterally with respect to the instrument channel within the housing from the second position to the first position to lock axial movement of the instrument relative to the housing.

27. A coupling device, comprising:

a housing having an instrument channel and a clamp;

a slider movable relative to the housing between a first position in which an engagement feature of the slider is disposed in the instrument channel and a second position in which the engagement feature is offset from the instrument channel, and an ejector;

wherein insertion of an instrument into the instrument channel displaces the ejector to causes the clamp to translate longitudinally within the housing to lock radial movement of the instrument relative to the housing, wherein displacement of the ejector from the instrument channel causes the slider to move from the second position to the first position, wherein the clamp translates longitudinally within the housing to lock axial movement of the instrument relative to the housing.

* * * * *